United States Patent
Fine et al.

(10) Patent No.: US 10,768,078 B2
(45) Date of Patent: *Sep. 8, 2020

(54) SAMPLE PROCESSING IMPROVEMENTS FOR QUANTITATIVE MICROSCOPY

(71) Applicant: Alentic Microscience Inc., Halifax (CA)

(72) Inventors: Alan Marc Fine, Prospect (CA); Hershel Macaulay, Bedford (CA)

(73) Assignee: Alentic Microscience Inc., Halifax NS ( * ) Notice: Subject to any disclaimer, the term of this patent is extended or adjusted under 35 U.S.C. 154(b) by 0 days.

This patent is subject to a terminal disclaimer.

(21) Appl. No.: 16/367,791

(22) Filed: Mar. 28, 2019

(65) Prior Publication Data

US 2019/0242794 A1 Aug. 8, 2019

Related U.S. Application Data

(63) Continuation of application No. 15/066,065, filed on Mar. 10, 2016, now Pat. No. 10,502,666, which is a
(Continued)

(51) Int. Cl.
*G01N 1/28* (2006.01)
*G01N 33/49* (2006.01)
(Continued)

(52) U.S. Cl.
CPC ............. *G01N 1/2813* (2013.01); *G01N 1/38* (2013.01); *G01N 21/31* (2013.01); *G01N 33/49* (2013.01);
(Continued)

(58) Field of Classification Search
CPC ........ G01N 1/2813; G01N 21/31; G01N 1/38; G01N 2201/068; G01N 2201/12;
(Continued)

(56) References Cited

U.S. PATENT DOCUMENTS 3,000,049 A 9/1961 Terry
3,447,863 A 6/1969 Patterson
(Continued)

FOREIGN PATENT DOCUMENTS

CA 2778837 5/2011
CN 102713720 A 10/2012
(Continued)

OTHER PUBLICATIONS

International Search Report and Written Opinion from corresponding PCT application No. PCT/US2010/054240 dated Dec. 27, 2010 (16 pages).
(Continued)

*Primary Examiner* — Sang H Nguyen
(74) *Attorney, Agent, or Firm* — Fish & Richardson P.C.

(57) ABSTRACT

Among other things, a diluted sample is generated based on mixing a small sample of blood with a one or more diluents. A thin film of the diluted sample is formed on the surface of a contact optical microscopy sensor. Red blood cells within a portion of the thin film of the diluted sample are illuminated using light of a predetermined wavelength. One or more images of the diluted sample are acquired based on illuminating the red blood cells within the portion of the thin film of the diluted sample. The acquired one or more images of the diluted sample are then processed. The mean corpuscular hemoglobin in the red blood cells within the portion of the thin film of the diluted sample is determined based on processing the acquired images of the diluted sample.

16 Claims, 2 Drawing Sheets

Related U.S. Application Data continuation-in-part of application No. 14/314,743, filed on Jun. 25, 2014, now Pat. No. 9,518,920, and a continuation-in-part of application No. 14/173,500, filed on Feb. 5, 2014.

(60) Provisional application No. 62/131,164, filed on Mar. 10, 2015, provisional application No. 61/839,735, filed on Jun. 26, 2013, provisional application No. 61/785,762, filed on Mar. 14, 2013, provisional application No. 61/761,467, filed on Feb. 6, 2013.

(51) Int. Cl.
- *G02B 21/36* (2006.01)
- *G02B 21/00* (2006.01)
- *G01N 1/38* (2006.01)
- *G01N 21/31* (2006.01)

(52) U.S. Cl.
CPC ....... *G02B 21/0008* (2013.01); *G02B 21/365* (2013.01); *G01N 2001/386* (2013.01); *G01N 2201/068* (2013.01); *G01N 2201/12* (2013.01)

(58) Field of Classification Search
CPC ............. G01N 2001/386; G01N 33/49; G02B 21/365; G02B 21/0008
See application file for complete search history.

(56) References Cited

U.S. PATENT DOCUMENTS

| | | |
|---|---|---|
| 3,551,023 A | 12/1970 | Brackett |
| 3,556,633 A | 1/1971 | Mutschmann et al. |
| 4,338,024 A | 7/1982 | Bolz et al. |
| 4,612,614 A | 9/1986 | Deindoerfer et al. |
| 4,658,471 A | 4/1987 | Nakanishi |
| 4,682,887 A | 7/1987 | Bellhouse |
| 4,744,643 A | 5/1988 | Taylor |
| 4,758,083 A | 7/1988 | Bellhouse |
| 4,845,809 A | 7/1989 | Pillifant |
| 4,882,284 A | 11/1989 | Kirchanski et al. |
| 4,950,455 A | 8/1990 | Smith |
| 4,963,498 A | 10/1990 | Hillman et al. |
| 5,039,487 A | 8/1991 | Smith |
| 5,181,382 A | 1/1993 | Middlebrook |
| 5,218,211 A | 6/1993 | Cresswell et al. |
| 5,307,161 A | 4/1994 | Miyamoto |
| 5,365,114 A | 11/1994 | Tsurushima et al. |
| 5,389,779 A | 2/1995 | Betzig et al. |
| 5,464,752 A | 11/1995 | Kortright et al. |
| 5,605,813 A | 2/1997 | Stevens |
| 5,612,223 A | 3/1997 | Kim et al. |
| 5,627,041 A | 5/1997 | Shartle |
| 5,633,972 A | 5/1997 | Walt et al. |
| 5,653,939 A | 8/1997 | Hollis et al. |
| 5,739,527 A | 4/1998 | Hecht et al. |
| 5,851,489 A | 12/1998 | Wolf et al. |
| 5,858,189 A | 1/1999 | Williams |
| 5,880,830 A | 3/1999 | Schechter |
| 5,894,349 A | 4/1999 | Harris et al. |
| 5,932,428 A | 8/1999 | Dubrow et al. |
| 6,083,763 A | 7/2000 | Balch |
| 6,084,683 A | 7/2000 | Bruno et al. |
| 6,104,495 A | 8/2000 | Sieben et al. |
| 6,180,314 B1 | 1/2001 | Berndt |
| 6,259,104 B1 | 7/2001 | Baer |
| 6,280,586 B1 | 8/2001 | Wolf et al. |
| 6,297,025 B1 | 10/2001 | Sugihara et al. |
| 6,302,985 B1 | 10/2001 | Takahashi et al. |
| 6,312,960 B1 | 11/2001 | Balch et al. |
| 6,323,944 B1 | 11/2001 | Xiao |
| 6,387,707 B1 | 5/2002 | Seul et al. |
| 6,396,980 B1 | 5/2002 | Liu et al. |
| 6,411,434 B1 | 6/2002 | Eastman |
| 6,432,720 B2 | 8/2002 | Chow |
| 6,470,532 B2 | 10/2002 | Rude |
| 6,506,664 B1 | 1/2003 | Beyne et al. |
| 6,621,079 B1 | 9/2003 | Shao et al. |
| 6,690,464 B1 | 2/2004 | Lewis et al. |
| 6,723,290 B1 | 4/2004 | Wardlaw |
| 6,773,676 B2 | 8/2004 | Schembri |
| 6,784,982 B1 | 8/2004 | Blumenfeld et al. |
| 6,803,238 B1 | 10/2004 | Eggers |
| 6,844,150 B2 | 1/2005 | Weiss et al. |
| 6,867,851 B2 | 3/2005 | Blumenfeld et al. |
| 6,901,086 B2 | 5/2005 | Li |
| 7,009,172 B2 | 3/2006 | Publicover et al. |
| 7,023,563 B2 | 4/2006 | Li |
| 7,079,256 B2 | 7/2006 | Li |
| 7,142,571 B2 | 11/2006 | Li |
| 7,151,246 B2 | 12/2006 | Fein et al. |
| 7,153,720 B2 | 12/2006 | Augusto |
| 7,280,222 B2 | 10/2007 | Li |
| 7,310,151 B2 | 12/2007 | Li |
| 7,326,930 B2 | 2/2008 | Crawely |
| 7,385,175 B2 | 6/2008 | Li et al. |
| 7,423,766 B1 | 9/2008 | Li |
| 7,425,460 B2 | 9/2008 | Pain |
| 7,443,507 B2 | 10/2008 | Ran |
| 7,466,409 B2 | 12/2008 | Scherer et al. |
| 7,476,787 B2 | 1/2009 | Thomas et al. |
| 7,518,731 B2 | 4/2009 | Li |
| 7,524,459 B2 | 4/2009 | Adams et al. |
| 7,626,695 B2 | 12/2009 | Betzig et al. |
| 7,651,598 B2 | 1/2010 | Shapiro et al. |
| 7,693,571 B2 | 4/2010 | Arnone et al. |
| 7,719,685 B2 | 5/2010 | Li |
| 7,727,752 B2 | 6/2010 | Klink et al. |
| 7,738,945 B2 | 6/2010 | Fauver et al. |
| 7,751,048 B2 | 7/2010 | Yang et al. |
| 7,773,227 B2 | 8/2010 | Yang et al. |
| 7,792,246 B2 | 9/2010 | Rodenburg et al. |
| 7,796,797 B2 | 9/2010 | Nakaya et al. |
| 7,850,916 B2 | 12/2010 | Wardlaw |
| 7,936,501 B2 | 5/2011 | Smith et al. |
| 7,982,883 B2 | 7/2011 | Cui et al. |
| 7,990,539 B2 | 8/2011 | Li |
| 8,004,692 B2 | 8/2011 | Li |
| 8,027,083 B2 | 9/2011 | Smith et al. |
| 8,081,303 B2 | 12/2011 | Levine et al. |
| 8,089,630 B2 | 1/2012 | Davis et al. |
| 8,120,783 B2 | 2/2012 | Li |
| 8,314,933 B2 | 11/2012 | Cui |
| 8,345,227 B2 | 1/2013 | Zahniser et al. |
| 8,446,667 B2 | 5/2013 | Smith et al. |
| 8,456,633 B2 | 6/2013 | Lewis et al. |
| 8,477,294 B2 | 7/2013 | Zahniser et al. |
| 8,488,111 B2 | 7/2013 | Zahniser et al. |
| 8,506,909 B2 | 8/2013 | Sunwoldt |
| 9,041,790 B2 | 5/2015 | Fine |
| 9,052,523 B2 | 6/2015 | Eastman et al. |
| 9,075,225 B2 | 7/2015 | Fine |
| 9,083,857 B2 | 7/2015 | Winkleman |
| 9,133,507 B2 | 9/2015 | Testa |
| 9,304,280 B2 | 4/2016 | Gulari |
| 9,518,920 B2 | 12/2016 | Fine |
| 9,720,217 B2 | 8/2017 | Fine |
| 9,817,027 B2 | 11/2017 | Segura |
| 9,989,750 B2 | 6/2018 | Fine et al. |
| 10,114,203 B2 | 10/2018 | Fine et al. |
| 10,345,564 B2 | 7/2019 | Fine et al. |
| 10,459,213 B2 | 10/2019 | Fine et al. |
| 2001/0046702 A1 | 11/2001 | Schembri |
| 2001/0052930 A1 | 12/2001 | Adair |
| 2002/0147384 A1 | 10/2002 | Uchikubo |
| 2003/0007894 A1* | 1/2003 | Wang ............... B07C 5/34 422/82.05 |
| 2003/0073910 A1 | 4/2003 | Chance |
| 2004/0171076 A1 | 9/2004 | Dejneka |
| 2004/0219184 A1 | 11/2004 | Brown et al. |
| 2005/0048498 A1 | 3/2005 | Woudenberg et al. |
| 2005/0190286 A1 | 9/2005 | Kaduchak et al. |
| 2005/0271548 A1 | 12/2005 | Yang et al. |

(56) References Cited

U.S. PATENT DOCUMENTS

| | | |
|---|---|---|
| 2006/0217594 A1 | 9/2006 | Ferguson |
| 2006/0223165 A1 | 10/2006 | Chang et al. |
| 2006/0263888 A1 | 11/2006 | Fritz et al. |
| 2007/0025709 A1 | 2/2007 | Gladnick |
| 2007/0087442 A1 | 4/2007 | Wardlaw |
| 2007/0207061 A1 | 9/2007 | Yang et al. |
| 2007/0243117 A1 | 10/2007 | Wardlaw |
| 2007/0258096 A1 | 11/2007 | Cui et al. |
| 2008/0095312 A1 | 4/2008 | Rodenburg et al. |
| 2008/0144899 A1 | 6/2008 | Varma et al. |
| 2008/0194012 A1 | 8/2008 | Lee |
| 2008/0213804 A1 | 9/2008 | Erickson et al. |
| 2008/0259443 A1 | 10/2008 | Smith et al. |
| 2008/0259444 A1 | 10/2008 | Smith |
| 2008/0285040 A1 | 11/2008 | Fourkas et al. |
| 2008/0319298 A1 | 12/2008 | Huys |
| 2009/0072332 A1 | 3/2009 | Dekker |
| 2009/0093970 A1 | 4/2009 | Lewy |
| 2009/0163432 A1 | 6/2009 | Takamatsu et al. |
| 2009/0174936 A1 | 7/2009 | Olszak |
| 2009/0218527 A1 | 9/2009 | French |
| 2009/0220125 A1 | 9/2009 | Ren et al. |
| 2009/0225319 A1 | 9/2009 | Lee et al. |
| 2009/0233329 A1 | 9/2009 | Rodriguez et al. |
| 2009/0258338 A1 | 10/2009 | Zhang |
| 2010/0033561 A1 | 2/2010 | Hersee |
| 2010/0067827 A1 | 3/2010 | Ozcan et al. |
| 2010/0097599 A1 | 4/2010 | Lewis et al. |
| 2010/0178722 A1 | 7/2010 | de Graff |
| 2010/0233191 A1 | 9/2010 | Buckley |
| 2010/0248300 A1 | 9/2010 | Yoshida et al. |
| 2010/0290049 A1 | 11/2010 | Yang et al. |
| 2010/0296094 A1 | 11/2010 | Yang et al. |
| 2011/0001460 A1 | 1/2011 | Steinmetzer |
| 2011/0014606 A1 | 1/2011 | Steinmetzer |
| 2011/0037846 A1 | 2/2011 | Huang |
| 2011/0070606 A1 | 3/2011 | Winkelman et al. |
| 2011/0096157 A1 | 4/2011 | Fine et al. |
| 2011/0149280 A1 | 6/2011 | Juhl |
| 2011/0151502 A1 | 6/2011 | Kendall et al. |
| 2011/0164803 A1 | 7/2011 | Wang |
| 2011/0181884 A1 | 7/2011 | Cui et al. |
| 2011/0190613 A1* | 8/2011 | Zhang .................. A61B 5/1455 600/328 |
| 2011/0205535 A1* | 8/2011 | Soller ................ A61B 5/14552 356/300 |
| 2011/0211058 A1 | 9/2011 | McCollum et al. |
| 2011/0234757 A1 | 9/2011 | Zheng et al. |
| 2011/0249109 A1 | 10/2011 | Fine |
| 2011/0254533 A1 | 10/2011 | Gong |
| 2012/0218379 A1 | 8/2012 | Ozcan |
| 2012/0223217 A1 | 9/2012 | Zheng et al. |
| 2012/0223291 A1 | 9/2012 | Klem et al. |
| 2012/0224053 A1 | 9/2012 | Vykoukal |
| 2012/0231533 A1 | 9/2012 | Holl |
| 2013/0002847 A1 | 1/2013 | Zahniser et al. |
| 2013/0052331 A1 | 2/2013 | Kram et al. |
| 2013/0217065 A1 | 8/2013 | Neef |
| 2014/0002662 A1 | 1/2014 | Lewis et al. |
| 2014/0152801 A1 | 6/2014 | Fine et al. |
| 2014/0268319 A1 | 9/2014 | Gulari |
| 2015/0002834 A1 | 1/2015 | Fine et al. |
| 2015/0241377 A1* | 8/2015 | Yano .................. C12Q 1/006 204/403.04 |
| 2015/0241679 A1 | 8/2015 | Fine et al. |
| 2016/0041200 A1 | 2/2016 | Fine |
| 2016/0187235 A1 | 6/2016 | Fine et al. |
| 2016/0356999 A1 | 12/2016 | Fine |
| 2017/0075099 A1 | 3/2017 | Fine et al. |
| 2017/0322402 A1 | 11/2017 | Fine et al. |
| 2018/0181884 A1 | 6/2018 | Rolle et al. |
| 2018/0284416 A1 | 10/2018 | Fine |
| 2019/0094509 A1 | 3/2019 | Fine |
| 2019/0293524 A9 | 9/2019 | Fine |
| 2019/0317309 A1 | 10/2019 | Fine |
| 2019/0324258 A1 | 10/2019 | Fine |

FOREIGN PATENT DOCUMENTS

| | | |
|---|---|---|
| CN | 105765440 | 7/2016 |
| CN | 105974571 A | 9/2016 |
| DE | 102011117228 | 5/2013 |
| EP | 0170565 | 2/1986 |
| EP | 1756260 | 2/2007 |
| EP | 2012114 | 1/2009 |
| EP | 2330215 A1 | 6/2011 |
| EP | 2494400 | 9/2012 |
| EP | 2554987 A1 | 2/2013 |
| EP | 2954310 | 12/2015 |
| EP | 3014330 | 5/2016 |
| EP | 3268737 | 1/2018 |
| JP | S58-182267 | 10/1983 |
| JP | 59-048954 | 3/1984 |
| JP | S62-262001 | 11/1987 |
| JP | S63-229426 | 9/1988 |
| JP | S64-71172 | 3/1989 |
| JP | 4-316478 | 11/1992 |
| JP | 5-219937 | 8/1993 |
| JP | 5243790 | 9/1993 |
| JP | H09-021963 | 1/1997 |
| JP | 11-64215 | 3/1999 |
| JP | 2000-146910 | 5/2000 |
| JP | 2001-78175 | 3/2001 |
| JP | 2002-525587 | 8/2002 |
| JP | 2004503223 | 2/2004 |
| JP | 2006-003653 | 1/2006 |
| JP | 2007536541 | 12/2007 |
| JP | 2008-501999 | 1/2008 |
| JP | 2008-192813 | 8/2008 |
| JP | 2009-65178 | 3/2009 |
| JP | 2009515155 | 4/2009 |
| JP | 2011-513794 | 4/2011 |
| JP | 2011515681 | 5/2011 |
| JP | 5059882 | 10/2012 |
| JP | 2013-507630 | 3/2013 |
| JP | 2013-509618 | 3/2013 |
| JP | 2013509618 | 3/2013 |
| JP | 2015-215624 | 12/2015 |
| JP | 2018-028683 | 2/2018 |
| WO | WO2000/012123 | 3/2000 |
| WO | WO2005/121749 | 12/2005 |
| WO | WO2008/112416 | 9/2008 |
| WO | WO 2008/136007 | 11/2008 |
| WO | WO 2006/133360 | 9/2009 |
| WO | WO2009/111573 | 9/2009 |
| WO | WO2009/111577 | 9/2009 |
| WO | WO 2010/148252 | 12/2010 |
| WO | WO2011/053631 | 5/2011 |
| WO | WO 2012/019118 | 2/2012 |
| WO | WO 2012/030313 | 3/2012 |
| WO | WO 2012/064873 | 5/2012 |
| WO | WO 2012/094523 | 7/2012 |
| WO | WO 2012/174542 | 12/2012 |
| WO | WO 2013/071352 | 5/2013 |
| WO | WO 2014/121388 | 8/2014 |
| WO | WO2014/205576 | 12/2014 |
| WO | WO2016/141487 | 9/2016 |

OTHER PUBLICATIONS

Ji, Honghao, et al., "Contact Imaging: Stimulation and Experiment", IEEE Transactions on Circuits and Systems—I: Regular Papers, vol. 54, No. 8, Aug. 2007 (13 pages).

Bayer, Manfred E. and John L. Sloyer, Jr., "The electrophoretic mobility of Gram-negative and Gram-positive bacteria: an electrokinetic analysis", Jan. 31, 1990 (8 pages).

Cook, G.M.W., "Glycoproteins in Membranes", Biol. Rev. (1968) 43, pp. 363-391, Jan. 1968 (29 pages).

Kiuchi, Masato and Akiyoshi Chayahara, "Titanium nitride for transparent conductors", Appl. Phys. Lett. 64(8), Feb. 21, 1994 (3 pages).

(56) References Cited

OTHER PUBLICATIONS

Alpha MED Scientific, Inc., "MED64: A low-noise multi-electrode array system for in vitro extracellular electrophysiology", MED64 product information, www.med64.com, received Jan. 31, 2012 (16 pages).
OmniVision, "The World's First ¼-inch 5-Megapixel SoC Image Sensor with OmniBSI™ Technology", OV5642, version 1.1, Dec. 2009 (2 pages).
International Preliminary Report on Patentability from corresponding PCT application No. PCT/US2010/054240 dated May 10, 2012 (7 pages).
European Communication for EP application No. 10827423.4 dated Jun. 6, 2012 (2 pages).
Zheng, et al., "Supporting Information", SI Text, www.pnas.org/cgi/doi/10.1073/pnas.1110681108, 2011, 3 pages.
Adams ML, Enzelberger M, Quake S, Scherer A. Microfluidic integration on detector arrays for absorption and fluorescence micro-spectrometers. Sensors and Actuators A: Physical. 2003;104(1):25-31. doi: 10.1016/S0924-4247(02)00477-6.
Adams M, DeRose G, Quake SR, Scherer A. Fundamental approach for optoelectronic and microfluidic integration for miniaturizing spectroscopic devices. 2002:1-6. doi: 10.1117/12.469818.
Alkaisi MM, Blaikie RJ, McNab SJ, Cheung R, Cumming DRS. Sub-diffraction-limited patterning using evanescent near-field optical lithography. Appl Phys Lett. 1999;75(22):3560-3562. http://dx.doi.org/10.1063/1.125388. doi: 10.1063/1.125388.
Allier CP, Hiernard G, Poher V, Dinten JM. Bacteria detection with thin wetting film lensless imaging. Biomed Opt Express. 2010;1(3):762-770. doi: 10.1364/BOE.1.000762.
Beese L, Feder R, Sayre D. Contact x-ray microscopy. A new technique for imaging cellular fine structure. Biophys J. 1986;49(1):259-268. doi: 10.1016/S0006-3495(86)83639-6.
Beiderman M, Tam T, Fish A, Jullien GA, Yadid-Pecht O. A low-light CMOS contact imager with an emission filter for biosensing applications. Biomedical Circuits and Systems, IEEE Transactions on. 2008;2(3):193-203. doi: 10.1109/TBCAS.2008.2001866.
Bishara W, Su T, Coskun AF, Ozcan A. Lensfree on-chip microscopy over a wide field-of-view using pixel super-resolution. Opt Express. 2010;18(11):11181-11191. http://www.opticsexpress.org/abstract.cfm?URI=oe-18-11-11181.
Coskun AF, Sencan I, Su T, Ozcan A. Lensless wide-field fluorescent imaging on a chip using compressive decoding of sparse objects. Opt Express. 2010;18(10):10510-10523. http://www.opticsexpress.org/abstract.cfm?URI=oe-18-10-10510.
Cui X, Lee LM, Heng X, et al. Lensless high-resolution on-chip optofluidic microscopes for caenorhabditis elegans and cell imaging. Proceedings of the National Academy of Sciences. 2008. doi: 10.1073/pnas.0804612105.
D.C. Ng, Nakagawa T, Mizuno T, et al. Integrated in vivo neural imaging and interface CMOS devices: Design, packaging, and implementation. IEEE Sens J. 2008;8(1):121-130. http://pubget.com/paper/pgtmp_3c74d9653c84d6253dff533a781220fb. doi: 10.1109/JSEN.2007.912921.
Dattner Y, Yadid-Pecht O. Low light CMOS contact imager with an integrated poly-acrylic emission filter for fluorescence detection. Sensors (Basel). 2010;10(5):5014-5027. doi: 10.3390/s100505014; 10.3390/s100505014.
Eggers, M. et al, "A Microchip for Quantitative Detection of Molecules Utilizing Luminescent and Radioisotope Reporter Groups", 516 BioFeature, vol. 17, No. 3, 1994 (8 pages).
Faulkner HML, Rodenburg JM. Movable aperture lensless transmission microscopy: A novel phase retrieval algorithm. Phys Rev Lett. 2004;93(2):023903. http://link.aps.org/doi/10.1103/PhysRevLett.93.023903.
Feder R, Costa JL, Chaudhari P, Sayre D. Improved detail in biological soft X-ray microscopy: Study of blood platelets. Science. 1981;212(4501):1398-1400.
Fischer UC, Zingsheim HP. Submicroscopic contact imaging with visible light by energy transfer. Applied Physics Letters. 1982;40(3):195-197. doi: 10.1063/1.93050.

Greenbaum A, Luo W, Su TW, et al. Imaging without lenses: Achievements and remaining challenges of wide-field on-chip microscopy. Nat Methods. 2012;9(9):889-895. doi: 10.1038/nmeth.2114; 10.1038/nmeth.2114.
Gurkan U, Moon S, Geckil H, et al. Miniaturized lensless imaging systems for cell and microorganism visualization in point-of-care testing. Biotechnol J. 2011;6(2):138-149. http://europepmc.org/abstract/MED/2129880.
Heng X, Erickson D, Baugh LR, et al. Optofluidic microscopy—a method for implementing a high resolution optical microscope on a chip. Lab Chip. 2006;6(10):1274-1276. http://dx.doi.org/10.1039/B604676B. doi: 10.1039/B604676B.
Heng X, Erickson D, Psaltis D, Yang C. A new imaging method: Optofluidic microscopy. . 2005:60030F-60030F. doi: 10.1117/12.632157.
Heng X, Hsiao E, Psaltis D, Yang C. An optical tweezer actuated, nanoaperture-grid based optofluidic microscope implementation method. Opt Express. 2007;15(25):16367-16375. http://www.opticsexpress.org/abstract.cfm?URI=oe-15-25-16367.
Ji, Honghao, Abshire PA, Urdaneta M, Smela E. CMOS contact imager for monitoring cultured cells. Circuits and Systems, 2005 ISCAS 2005 IEEE International Symposium on. 2005:3491-3494 vol. 4. doi: 10.1109/ISCAS.2005.1465381.
Ji, Honghao, Sander D, Haas A, Abshire PA. A CMOS contact imager for locating individual cells Circuits and Systems, 2006 ISCAS 2006 Proceedings 2006 IEEE International Symposium on. 2006:4 pp. doi: 10.1109/ISCAS.2006.1693345.
Ji, Honghao, Sander D, Haas A, Abshire PA. Contact imaging: Simulation and experiment. Circuits and Systems I: Regular Papers, IEEE Transactions on. 2007;54(8):1698-1710. doi: 10.1109/TCSI.2007.902409.
Isikman SO, Bishara W, Mavandadi S, et al. Lens-free optical tomographic microscope with a large imaging volume on a chip. Proceedings of the National Academy of Sciences. 2011. doi: 10.1073/pnas.1015638108.
Isikman SO, Sencan I, Mudanyali O, Bishara W, Oztoprak C, Ozcan A. Color and monochrome lensless on-chip imaging of caenorhabditis elegans over a wide field-of-view. Lab Chip. 2010;10(9):1109-1112. http://dx.doi.org/10.1039/C001200A. doi: 10.1039/C001200A.
Kobayashi T, Tamura H, Hatanaka Y, et al. Functional neuroimaging by using an implantable CMOS multimodal device in a freely-moving mouse. Biomedical Circuits and Systems Conference (BioCAS), 2011 IEEE 2011:110-113. doi: 10.1109/BioCAS.2011.6107739.
Lange D, Storment CW, Conley CA, Kovacs GTA. A microfluidic shadow imaging system for the study of the nematode *Caenorhabditis elegans* in space. Sensors Actuators B: Chem. 2005;107(2):904-914. doi: 10.1016/j.snb.2004.12.039.
Lee L, Cui X, Yang C. The application of on-chip optofluidic microscopy for imaging giardia lamblia trophozoites and cysts. Biomed Microdevices. 2009;11(5):951-958. http://dx.doi.org/10.1007/s10544-009-9312-x. doi: 10.1007/s10544-009-9312-x.
Lee M, Yaglidere O, Ozcan A. Field-portable reflection and transmission microscopy based on lensless holography. Biomed Opt Express. 2011;2(9):2721-2730. doi: 10.1364/BOE.2.002721; 10.1364/BOE.2.002721.
Lee SA, Zheng G, Mukherjee N, Yang C. On-chip continuous monitoring of motile microorganisms on an ePetri platform. Lab Chip. 2012;12(13):2385-2390. doi: 10.1039/c2lc40090a; 10.1039/c2lc40090a.
Lorenz KS, Salama P, Dunn KW, Delp EJ. Digital correction of motion artefacts in microscopy image sequences collected from living animals using rigid and nonrigid registration. J Microsc.2012;245(2):148-160. doi: 10.1111/j.1365-2818.2011.03557.x; 2012.
Maiden AM, Rodenburg JM. An improved ptychographical phase retrieval algorithm for diffractive imaging. Ultramicroscopy. 2009;109(10):1256-1262. doi: 10.1016/j.ultramic.2009.05.012.
Maiden AM, Rodenburg JM, Humphry MJ. Optical ptychography: A practical implementation with useful resolution. Opt Lett. 2010;35(15):2585-2587. http://ol.osa.org/abstract.cfm?URI=ol-35-15-2585.

(56) References Cited

OTHER PUBLICATIONS

Manaresi N, Romani A, Medoro G, et al. A CMOS chip for individual cell manipulation and detection. Solid-State Circuits, IEEE Journal of. 2003;38(12):2297-2305. doi: 10.1109/JSSC.2003.819171.

McCorkle R, Angilello J, Coleman G, Feder R, LA Placa SJ. Flash X-ray microscopy. Science. 1979;205(4404):401-402. doi: 10.1126/science.205.4404.401.

Milanfar P (2010) Super-Resolution Imaging (CRC Press, Boca Raton, FL).

Moon S, Keles HO, Ozcan A, et al. Integrating microfluidics and lensless imaging for point-of-care testing. Biosensors and Bioelectronics. 2009;24(11):3208-3214. doi: 10.1016/j.bios.2009.03.037.

Moscelli N, van den Driesche S, Witarski W, Pastorekova S, Vellekoop MJ. An imaging system for real-time monitoring of adherently grown cells. Sensors and Actuators A: Physical. 2011;172(1):175-180. doi: 10.1016/j.sna.2011.05.010.

Mudanyali O, Tseng D, Oh C, et al. Compact, light-weight and cost-effective microscope based on lensless incoherent holography for telemedicine applications. Lab Chip. 2010;10(11):1417-1428. http://dx.doi.org/10.1039/C000453G. doi: 10.1039/C000453G.

Ng DC, Tokuda T, Nakagawa T, et al. A new neural imaging approach using a CMOS imaging device. Conf Proc IEEE Eng Med Biol Soc. 2006;1:1061-1064. doi: 10.1109/IEMBS.2006.260316.

Ng DC, Tamura H, Mizuno T, et al. An implantable and fully integrated complementary metal-oxide semiconductor device for in vivo neural imaging and electrical interfacing with the mouse hippocampus. Sensors and Actuators A: Physical. 2008;145-146(0):176-186. doi: 10.1016/j.sna.2007.11.020.

Ng, D, Tokuda T, Shiosaka S, Tano Y, Ohta J. Implantable microimagers. Sensors. 2008;8(5):3183-3204. http://www.mdpi.com/1424-8220/8/5/3183.

Oh C, Isikman SO, Khademhosseinieh B, Ozcan A. On-chip differential interference contrast microscopy using lensless digital holography. Opt Express. 2010;18(5):4717-4726. http://www.opticsexpress.org/abstract.cfm?URI=oe-18-5-4717.

Ohta J, Tagawa A, Minami H, et al. A multimodal sensing device for fluorescence imaging and electrical potential measurement of neural activities in a mouse deep brain. Engineering in Medicine and Biology Society, 2009 EMBC 2009 Annual International Conference of the IEEE. 2009:5887-5890. doi: 10.1109/IEMBS.2009.5334461.

Pang S, Han C, Kato M, Sternberg PW, Yang C. Wide and scalable field-of-view talbot-grid-based fluorescence microscopy. Opt Lett. 2012;37(23):5018-5020. doi: 10.1364/OL.37.005018.

Prakash SB, Nelson NM, Haas AM, et al. BioLabs-on-a-chip: Monitoring cells using CMOS biosensors. Life Science Systems and Applications Workshop, 2006 IEEE/NLM. 2006:1-2. doi: 10.1109/LSSA.2006.250426.

Psaltis D, Quake SR, Yang C. Developing optofluidic technology through the fusion of microfluidics and optics. Nature. 2006;442(7101):381-386. http://dx.doi.org/10.1038/nature05060.

Reale L, Bonfigli F, Lai A, et al. X-ray microscopy of plant cells by using LiF crystal as a detector. Microsc Res Tech. 2008;71(12):839-848. http://europepmc.org/abstract/MED/18785247.

Richard C, Renaudin A, Aimez V, Charette PG. An integrated hybrid interference and absorption filter for fluorescence detection in lab-on-a-chip devices. Lab Chip. 2009;9(10):1371-1376. doi: 10.1039/b819080a; 10.1039/b819080a.

Rodenburg JM, Hurst AC, Cullis AG. Transmission microscopy without lenses for objects of unlimited size. Ultramicroscopy. 2007;107(2-3):227-231. doi: 10.1016/j.ultramic.2006.07.007.

Salama K, Eltoukhy H, Hassibi A, El-Gamal A. Modeling and simulation of luminescence detection platforms. Biosens Bioelectron. 2004;19(11):1377-1386. doi: 10.1016/j.bios.2003.12.031.

Sander D, Dandin M, Honghao Ji, Nelson N, Abshire P. Low-noise CMOS fluorescence sensor Circuits and Systems, 2007 ISCAS 2007 IEEE International Symposium on. 2007:2007-2010. doi: 10.1109/ISCAS.2007.378431.

Seo S, Su T, Tseng DK, Erlinger A, Ozcan A. Lensfree holographic imaging for on-chip cytometry and diagnostics. Lab Chip. 2009;9(6):777-787. http://dx.doi.org/10.1039/B813943A. doi: 10.1039/B813943A.

Singh RR, Ho D, Nilchi A, Genov R, Gulak PG. A hybrid thin-film/CMOS fluorescence contact imager. Circuits and Systems, 2009 ISCAS 2009 IEEE International Symposium on. 2009:2437-2440. doi: 10.1109/ISCAS.2009.5118293.

Singh RR, Ho D, Nilchi A, Gulak PG, Yau P, Genov R. A CMOS/Thin-film fluorescence contact imaging microsystem for DNA analysis. Circuits and Systems I: Regular Papers, IEEE Transactions on. 2010;57(5):1029-1038. doi: 10.1109/TCSI.2010.2043990.

Singh RR, Leng L, Guenther A, Genov R. A hybrid CMOS-microfluidic contact imaging microsystem. . 2009:739712-739712. doi: 10.1117/12.827862.

Su TW, Seo S, Erlinger A, Ozcan A. High-throughput lensfree imaging and characterization of a heterogeneous cell solution on a chip. Biotechnol Bioeng. 2009;102(3):856-868. doi: 10.1002/bit.22116; 10.1002/bit.22116.

Tam T, Jullien GA, Yadid-Pecht O. A CMOS contact imager for cell detection in bio-sensing applications. Circuits and Systems, 2007 ISCAS 2007 IEEE International Symposium on. 2007:813-816. doi: 10.1109/ISCAS.2007.378030.

Tokuda T, Ng DC, Yamamoto A, Kagawa K, Nunoshita M, Ohta J. A CMOS optical/potential image sensor with 7.5 μm pixel size for on-chip neural and DNA spot sensing. Engineering in Medicine and Biology Society, 2005 IEEE-EMBS 2005 27th Annual International Conference of the. 2005:7269-7272. doi: 10.1109/IEMBS.2005.1616189.

Tseng D, Mudanyali O, Oztoprak C, et al. Lensfree microscopy on a cellphone. Lab Chip. 2010; 10(14):1787-1792. http://dx.doi.org/10.1039/C003477K. doi: 10.1039/C003477K.

Wang A, Gill P, Molnar A. Light field image sensors based on the talbot effect. Appl Opt. 2009;48(31):5897-5905. http://ao.osa.org/abstract.cfm?URI=ao-48-31-5897.

Zheng G, Lee SA, Yang S, Yang C. Sub-pixel resolving optofluidic microscope for on-chip cell imaging. Lab Chip. 2010;10(22):3125-3129. http://dx.doi.org/10.1039/C0LC00213E. doi: 10.1039/C0LC00213E.

Zheng G, Cui X, Yang C. Surface-wave-enabled Darkfield aperture for background suppression during weak signal detection. Proceedings of the National Academy of Sciences. 2010. doi: 10.1073/pnas.0912563107.

Zheng G, Lee SA, Antebi Y, Elowitz MB, Yang C. The ePetri dish, an on-chip cell imaging platform based on subpixel perspective sweeping microscopy (SPSM). Proceedings of the National Academy of Sciences. 2011. doi: 10.1073/pnas.1110681108.

Voluntary amendment filed with English translation of Chinese Application No. 201080059753.X filed Feb. 7, 2013 (17 pages).

Office action with English translation from Chinese Application No. 201080059753.X dated Dec. 25, 2013 (19 pages).

Response to European Communication dated Jun. 6, 2012 in European application No. 10827423.4, dated Dec. 10, 2012 (15 pages).

Lee, Seung Ah, et al., "Supplementary Information for: Sub-pixel resolving optofluidic microscope for on-hip cell imaging", Supplementary Material (ESI) for Lab on a Chip, The Royal Society of Chemistry, 2012 (4 pages).

Cetin, Arif E., et al., "Handheld high-throughput plasmonic bio sensor using computational on-chip imaging", Light: Science & Applications, e122, doi:10.1038/1sa.2014.3, 2014 (10 pages).

Office action with English translation dated Apr. 2, 2014 in Japanese application 2012-536989 (12 pages).

Entcheva, Emilia, et al., "Contact Fluorescence Imaging of Reentry in Monolayers of Cultured Neonatal Rat Ventricular Myocytes", Department of Biomedical Engineering, The Johns Hopkins. University School of Medicine, Baltimore, Maryland, Journal of Cardiovascular Electrophysiology, vol. 11, No. 6, pp. 665-676, Jun. 2000 (13 pages).

(56) References Cited

OTHER PUBLICATIONS

Entcheva, Emilia, et al. "Fluorescence Imaging of Electrical Activity in Cardia Cells Using an All-Solid-State System", IEEE Transactions on Biomedical Engineering, vol. 51, No. 2, pp. 333-341, Feb. 2004 (9 pages).
Entcheva, Emilia, et al, "Macroscopic optical mapping of excitation in cardiac cell networks with ultra-high spatiotemporal resolution", Progress in Biophysics & Molecular Biology, vol. 92, pp. 232-257, 2006 (26 pages).
Liu, Yingkai, et al., "Cell-lab on a chip: a CMOS-Based Microsystem for Culturing and Monitoring Cells", Proceedings of the 26th Annual International Conference of the IEEE EMBS, San Francisco, CA, pp. 2534-2537, Sep. 1-5, 2004 (4 pages).
Lu, Steven N., et al., "Optical Mapping of Anatomical Reentry in Monolayers of Cultured Neonatal Rat Cardiac Myocytes", Proceedings of the First Joint BMES/EMBS Conference, Serving Humanity, Advancing Technology, Oct. 13-16, 1999 (1 page).
Ng, David, et al., "Integrated In Vivo Neural Imaging and Interface CMOS Devices: Design, Packaging, and Implementation", IEEE Sensors Journal, vol. 8, No. 1, pp. 121-130, Jan. 2008. (10 pages).
Barda Broad Agency Announcement for the Addvanced Research and Development of Chemical, Biological, Radiological, and Nuclear Medical Countermeasures, "Development of a Rapid, Point-of-Care Biodosimeter to Determine Absorbed Radiation Dose", White Paper for Research Areas 6.1 and 6.2 (Biodosimetry Diagnostics), Jun. 7, 2013 (13 pages).
Zheng, Guoan, et al., "Scanning Projective Microscopy for 2D and 3D imaging", Electrical Engineering, California Institute of Technology, 2011 (5 pages).
Rojas-Palma, Carlos, "Triage, Monitoring and Treatment Handbook," 2009 (290 pages).
Certified PCT application No. PCT/JP2007/000401 filed Apr. 26, 2006 (22 pages).
Optofluidics, "Optofluidic microscope shrinks to fit on a chip", optics.org/ole, Oct. 2008 (2 pages).
Sadrozinski, Harmut F, et al., "The Particl Tracking Silicon Microscope PTSM", Nov. 15, 2003 (5 pages).
Cabello, Jorge, et al., "Digital autoradiography using room temperature CCD and CMOS imaging technology", Phys. Med. Biol. 52 (2007), 4993-5011 (19 pages).
Waselenko, Jamie K., "Medical Management of the Acute Radiation Syndrome: Recommendations of the Strategic National Stockpile Radiation Working Group", Annual Internal Medicine, 2004 (19 pages).
American Red Cross, "Planning Guidance for Response to a Nuclear Detonation", Jun. 2010 (135 pages).
Nakayama, Yasuhiro, "Varied Effects of Thoracic Irradiation on Peripheral Lymphocyte Subsets in Lung Cancer Patients", Internal Medicine vol. 34, No. 10, Oct. 1995 (7 pages).
Goans, Ronald E., et al., "Early Dose Assessment in Criticality Accidents", Health Physics Society, 2001 (4 pages).
Goans, Ronald E., et al., "Early Dose Assessment Following Severe Radiation Accidents", Health Physics, 72(4):513-518, Apr. 1997, abstract (1 page).
Baranov, AE., et al., "Chernobyl experience: biological indictors of exposure to ionizing radiation", Stem Cells, 13 Suppl 1:69-77, May 1995 (2 pages).
Koenig, Kristi L., et al., "Medical Treatment of Radiological Casualties: Current Concepts", Disaster and Terrorism/Review Article, Jan. 20, 2005 (10 pages).
Williams, Jacqueline P., "Animal Models for Medical Countermeasures to Radiation Exposure", National Institute of Health, Apr. 2010 (35 pages).
Ivashkevich, Alesia N. et al., "γH2AX foci as a measure of DNA damage: A computational approach to automatic analysis", Mutation Research 711, 49-60, 2011 (12 pages).
Farsiu, Sina, et al., "Multiframe Demosaicing and Super-Resolution of Color Images", IEEE Transactions on Image Processing, vol. 15, No. 1, Jan. 2006 (19 pages).

Vaurijoux, Aurelie, et al., "Biological Dosimetry of Ionizing Radiation", Laboratory of Biological Dosimetry, www.intechopen.com, Feb. 12, 2012 (21 pages).
Swartz, Harold, M., et al., "A Critical Assessment of Biodosimetry Methods for Large-Scale Incidents", vol. 98, No. 2, Feb. 2010 (14 pages).
Alexander, George A., et al., "BiodosEPR-2006 Meeting: Acute dosimetry consensus committee recommendations on biodosimetry applications in events involving uses of radiation by terrorists and radiation accidents", Science Direct, 2007 (25 pages).
Seo, Sungkyu, et al., "High-Throughput Lens-Free Blood Analysis on a Chip", Anal. Chem. 82, 4621-4627, 2010 (7 pages).
Mudanyali, Onur, et al., "Lenless On-Chip Imaging of Cells provides a new tool for high-throughout cell-biology and medical diagnostics", Journal of Visualized Experiments, 2009 (3 pages).
Webster, J.R., et al., "Monolithic Electrophoresis Device with Integrated Fluorescence Detector", Anal. Chem. 1622-1626, 2001 (5 pages).
Mudayali, Onur, et al., "Compact, light-weight and cost-effective microscope based on lensless incoherent holography for telemedicine applications", Lab on a Chip, 2010 (20 pages).
International Search Report and Written Opinion dated Jul. 17, 2014 from corresponding PCT Application No. PCT/CA2014/050070 (4 pages).
Baranov, A.E. et al., "Use of Blood Cell Count Changes after Radiation Exposure in Dose Assessment and Evaluation of Bone Marrow Function", Institute of Biophysics, Ministry of the USSR, Moscow, USSR, 1990 (17 pages).
Response to Office action with English translation from Chinese Application No. 201080059753.X dated Jul. 9, 2014 (12 pages).
Response with English translation to Japanese Office action filed in Japanese application 2012-536989 dated Sep. 30, 2014 (29 pages).
Chinese office action with English translation from Chinese Application 201080059753.X dated Nov. 17, 2014 (4 pages).
Response to Office action with English translation from Chinese application No. 201080059753.X dated Feb. 2, 2015 (13 pages).
Decision of Rejection with English translation from Japanese application 2012-536989 dated Mar. 2, 2015 (11 pages).
Chinese Office Action with English translation from Chinese application 201080059753.X dated May 7, 2015 (5 pages).
Japanese Notice of Reasons for Rejection, with translation thereof, for JP Appl No. 2015-132271, dated Aug. 1, 2016. (12 pages).
Chinese Office Action with English translation from Chinese application 201080059753.X dated Sep. 15, 2015. (6 pages).
Canadian Office Action from Canadian application 2778725 dated Nov. 22, 2016 (4 pages).
European Communication from European application 14749668.1 dated Nov. 7, 2016 (5 pages).
Chinese Office Action with English translation from Chinese application 201610217300.4 dated Aug. 30, 2017 (7 pages).
Response to Chinese Office Action in Chinese application 201610217300.4 dated Aug. 30, 2017, filed on Jan. 9, 2018 (12 pages).
European Supplemental Search Report issued in European application 10827423.4 dated Jul. 12, 2017 (19 pages).
Good, B.T., et al., "An effervescent reaction micropump for portable microfluidic systems", Lab on a Chip, Royal Society of Chemistry, vol. 6, No. 5, Jan. 1, 2006 (Jan. 1, 2006), pp. 659-666, XP002577744, ISSN: 1473-0197, DOI: 10.1O39/B601542E [retrieved on Mar. 20, 2006].
Ozcan, Aydogan: Lensfree on-chip imaging for telemedicine applications, Optical MEMS and Nanophotonics, 2009 IEEE/LEOS International Conference on, IEEE, Piscataway, NJ, USA, Aug. 17, 2009 (Aug. 17, 2009), pp. 59-60, XP031570125, ISBN: 978-1-4244-2382].
Ozcan, Aydogan et al.,: "Ultra-wide-field lens-free monitoring of cells on-chip", Lab on a Chip, vol. 8, No. 1, Jan. 1, 2008 (Jan. 1, 2008), p. 98, XP055051174, ISSN: 1473-0197, DOI: 10.1039/B713695A.
Su, Ting-Wei et al: "24: OPN 2008 Towards Wireless Health: On-Chip Cytometry", December Lensless 16,21-25, Dec. 30, 2008 (Dec. 30, 2008), XP055419182, Retrieved from the Internet: URL:https://www.osapublishing.org/DirectPDFAccess/472D83FE-

(56) References Cited

OTHER PUBLICATIONS

B727-F2F7-7A63B2F4FBF0B3AD_175086/opn-19-12-24.pdf?da=1&id=175086&seq=0&mobile=no [retrieved on Oct. 25, 2017].
European Communication issued in European application No. 10827423.4 dated Dec. 11, 2017. (13 pages).
Response to Japanese Notice of Reasons for Rejection, with English translation thereof, for JP Appl No. 2015-132271, dated Jan. 31, 2017 (29 pages).
Japanese Notice of Reasons for Rejection, with translation thereof, for JP Appl No. 2015-132271, dated Jun. 14, 2017. (17 pages).
Canadian Office Action issued in Canadian application 2938896 dated Jul. 11, 2017 (31 pages).
Response to Canadian Office Action submitted in Canadian application 2938896 on Jan. 11, 2018 (125 pages).
European Search Report issued in European application 14749668.1 dated Oct. 24, 2016 (6 pages).
Response to European Communication from European application 14749668.1 dated Feb. 21, 2017 (29 pages).
Japanese Office Action with English translation issued in Japanese application 2015-556353 dated Nov. 27, 2017 (14 pages).
International Preliminary Report on Patentability dated Aug. 20, 2015 from corresponding PCT Application No. PCT/CA2014/050070 (11 pages).
Isikman et al., "Lensfree computational microscopy tools for cell and tissue imaging at the point-of-care and in low-resource settings". Analytical Cellular Pathology, vol. 35 pp. 229-247, 2012.
Kim et al., "LED and CMOS image sensor based hemoglobin concentration measurement technique". Sensors and Actuators B, vol. 157, pp. 103-109, 2011.
Stybayeva et al., "Lensfree holographic imaging of antibody microarrays for high-throughput detection of leukocyte numbers and function". Analytical Chemistry, vol. 82(9): 3736-3744, 2010.
Lee et al., "Color capable sub-pixel resolving optofluidic microscope and its application to blood cell imaging for malaria diagnosis". PLOS ONE, vol. 6(10):e23427, 2011.
Mudanyali et al., "Compact and cost-effective lensless telemedicine microscopy for global health applications". IEEE Global Humanitarian Technology Conference, pp. 62+-65, 2011.
International Search Report and Written Opinion for corresponding PCT/CA2014/050610, dated Sep. 16, 2014.
International Preliminary Report on Patentability for corresponding PCT/CA2014/050610, dated Jan. 7, 2016.
Voluntary amendment with English translation filed in CN Application 201480047483.9 dated Jun. 27, 2016 (21 pages).
European Communication Pursuant to Rules 161(2) & 162 EPC issued in European application 14817587.0 dated Feb. 9, 2016 (2 pages).
Response to European Communication Pursuant to Rules 161(2) & 162 EPC issued in European application 14817587.0 dated Jun. 28, 2016 (5 pages).
Supplemental Search Report from European application 14817587.0 dated Jan. 26, 2017 (9 pages).
European Communication Pursuant to Rules 70(2) and 70a(2) EPC issued in European application.14817587.0 dated Feb. 14, 2017 (1 page).
Response to European Communication Pursuant to Rules 70(2) and 70a(2) EPC issued in European application 14817587.0 dated Aug. 18, 2017 (14 pages).
European Communication pursuant to Article 94(3) EPC issued in European Application 14817587.0 dated Oct. 26, 2017 (5 pages).
Japanese Office action issued in Japanese application 2016-522155 dated Feb. 19, 2018 (7 pages).
Response to Japanese Office action with English translation issued in Japanese application 2015-556353 dated Feb. 27, 2018 (8 pages).
Gabriel et al., "Inexpensive Integrated Device", Twelfth International Conference on Miniaturized Systems for Chemistry and Life Sciences Oct. 12-16, 2008, San Diego, California, USA (2 pages).
Canadian office action for Canadian application 2938896 dated Jul. 3, 2018 (20 pages).
Canadian office action for Canadian application 2953620 dated Nov. 8, 2017 (10 pages).
Response to Canadian office action for Canadian application 2953620 dated Apr. 13, 2018 (12 pages).
Chinese office action with English translation issued in Chinese application 201480047483.9 dated Dec. 5, 2017 (15 pages).
Response to Chinese office action with English translation for Chinese application 201480047483.9 dated Apr. 16, 2018 (14 pages).
Response to Japanese Office action issued in Japanese application 2016-522155 dated May 14, 2018 (14 pages).
Response to European Communication in European application No. 10827423.4 dated Apr. 5, 2018 (21 pages).
Office Action with English translation from Japanese application 2015-556353 dated Jul. 23, 2018 (8 pages).
Canadian office action from Canadian application 2778725, dated Jun. 12, 2018 (23 pages).
Response to Canadian office action in Canadian application 2778725, filed on Sep. 25, 2018.
Response to Chinese office action is Chinese application 201610217300.4 dated Jan. 9, 2018 (12 pages).
Chinese office action with English translation from Chinese application 201610217300.4 dated May 10, 2018 (15 pages).
Response to Chinese office action is Chinese application 201610217300.4 filed on Jun. 6, 2018 (12 pages).
Chinese office action with English translation from Chinese application 201610217300.4 dated Oct. 12, 2018 (8 pages).
Response to Chinese office action is Chinese application 201610217300.4 filed on Oct. 29, 2018 (6 pages).
Response to Office Action with English translation from Japanese application 2015-556353 filed on Sep. 28, 2018 (9 pages).
Canadian office action for Canadian application 2953620 dated Oct. 11, 2018 (7 pages).
Chinese office action with English translation issued in Chinese application 201480047483.9 dated Oct. 8, 2018 (17 pages).
Response to European Communication pursuant to Article 94(3) EPC in European Application 14817587.0 filed on Apr. 30, 2018 (10 pages).
Japanese Office action with English translation issued in Japanese application 2016-522155 dated Oct. 29, 2018 (8 pages).
European Extended Search Report from European application 16760984.1 dated Oct. 16, 2018 (9 pages).
European Communication from European application 16760984.1 dated Nov. 5, 2018 (1 page).
Japanese office action with English translation from Japanese application 2017-199014 dated Dec. 3, 2018 (20 pages).
Response to Canadian Office action dated Jul. 3, 2018 in Canadian application 2938896 filed on Dec. 24, 2018 (37 pages).
Su, Ting-wei et al, "High Throughout Lensfree Imaging and Characterization of a Heterogeneous Cell Solution on a chip", Biotechnology and Bioengineering, Sep. 8, 2008 (13 pages).
Response with English translation to Chinese office action issued in Chinese application 201480047483.9 dated Oct. 8, 2018, filed on Dec. 24, 2018 (16 pages).
Office Action with English translation from Japanese application 2015-556353 dated Feb. 18, 2019 (5 pages).
Transaction history of U.S. Appl. No. 61/255,781, filed Oct. 28, 2009 as of Feb. 26, 2018.
Transaction history of U.S. Appl. No. 12/913,639, filed Oct. 27, 2010.
Transaction history of U.S. Appl. No. 14/698,532, filed Apr. 28, 2015.
Transaction history and application as filed includes pending claims (2017/0322402) of U.S. Appl. No. 15/642,434, filed Jul. 6, 2017 as of Feb. 26, 2018.
Transaction history and issued claims (included in U.S. Pat. No. 9,075,225) of U.S. Appl. No. 13/095,175, filed Apr. 27, 2011 as of Feb. 26, 2018.
Transaction history, application as filed and pending claims of U.S. Appl. No. 14/710,046, filed May 12, 2015.
Transaction history and application as filed for U.S. Appl. No. 61/761,467, filed Feb. 6, 2013.

(56) References Cited

OTHER PUBLICATIONS

Transaction history and application as filed for U.S. Appl. No. 61/785,762, filed Mar. 14, 2013.
Transaction history, application as filed and pending claims of U.S. Appl. No. 14/173,500, filed Feb. 5, 2014, as of Feb. 26, 2018.
Transaction history and application as filed of U.S. Appl. No. 61/839,735, filed Jun. 26, 2013.
Transaction history, application as filed and issued claims (included in U.S. Pat. No. 9,518,920) of U.S. Appl. No. 14/314,743, filed Jun. 25, 2014 as of Mar. 5, 2018.
Transaction history, application as filed (included in Published application 2017/0075099) and pending claims of U.S. Appl. No. 15/360,724, filed Nov. 23, 2016 as of Mar. 5, 2018.
Transaction history and application as filed for U.S. Appl. No. 62/131,164, filed Mar. 10, 2015 as of Feb. 26, 2018.
Transaction history and application as filed with pending claims (included in 2016/0187235) for U.S. Appl. No. 15/066,065, filed Mar. 10, 2016 as of Feb. 26, 2018.
Mustafa Mir et al., "Blood testing at the single cell level using quantitative phase and amplitude microscopy", Biomedical Optics Express, vol. 2, No. 12; Dec. 1, 2011.
USPTO Transaction history, application as filed for U.S. Appl. No. 12/913,639.
USPTO Transaction history, application as filed for U.S. Appl. No. 13/095,175.
USPTO Transaction history, application as filed for U.S. Appl. No. 14/173,500.
USPTO Transaction history, application as filed for U.S. Appl. No. 14/314,743.
USPTO Transaction history, application as filed for U.S. Appl. No. 14/698,532.
USPTO Transaction history, application as filed for U.S. Appl. No. 14/710,046.
USPTO Transaction history, application as filed for U.S. Appl. No. 15/066,065.
USPTO Transaction history, application as filed for U.S. Appl. No. 15/360,724.
USPTO Transaction history, application as filed for U.S. Appl. No. 15/642,434.
USPTO Transaction history, application as filed for U.S. Appl. No. 15/995,598.
USPTO Transaction history, application as filed for U.S. Appl. No. 16/113,578.
YongKeum Park et al., "Spectroscopic phase microscopy for quantifying hemoglobin concentrations in intact red blood cells", Opt Lett. Dec. 1, 2009; 34(23): 3668-3670.
U.S. Appl. No. 12/913,639, filed Oct. 27, 2010 U.S. Pat. No. 9,041,790, Issued, U.S. Pat. No. 9,041,790 submitted on Mar. 28, 2019.
U.S. Appl. No. 14/698,532, filed Apr. 28, 2015 U.S. Pat. No. 9,720,217, Issued.
U.S. Appl. No. 15/642,434, filed Jul. 6, 2017 U.S. Pat. No. 10,114,203 Issued, U.S. Pat. No. 10,114,203 submitted on Mar. 28, 2019.
U.S. Appl. No. 16/113,578, filed Aug. 27, 2018 Pending.
U.S. Appl. No. 13/095,175, filed Apr. 27, 2011 U.S. Pat. No. 9,075,225, Issued U.S. Pat. No. 9,075,225 submitted on Mar. 28, 2019.
U.S. Appl. No. 14/710,046, filed May 12, 2015 Pending, No. 20160041200 submitted on Mar. 28, 2019.
U.S. Appl. No. 14/173,500, filed Feb. 5, 2014 Pending, No. 20140152801 submitted on Mar. 28, 2019 .
U.S. Appl. No. 14/314,743, filed Jun. 25, 2014 U.S. Pat. No. 9,518,920, Issued, U.S. Pat. No. 9,518,920 submitted on Mar. 28, 2019.
U.S. Appl. No. 15/360,724, filed Nov. 23, 2016 U.S. Pat. No. 9,989,750 Issued, U.S. Pat. No. 9,989,750 submitted on Mar. 28, 2019.
U.S. Appl. No. 15/995,598, filed Jun. 1, 2018 Pending, No. 20180284416 submitted on Mar. 28, 2019.

U.S. Appl. No. 15/066,065, filed Mar. 10, 2016 Pending, No. 20160187235 submitted on Mar. 28, 2019.
Canadian Office Action for Canadian application 2938896, dated Jul. 23, 2019 (4 pages).
Chinese Office Action with English translation in Chinese Application No. 201910089876.0, dated Nov. 28, 2019, 10 pages.
Japanese Notice of Reasons for Rejection, with English Translation, for Japanese Application No. 2017-199014, dated Sep. 10, 2019, 9 pages.
Japanese Notice of Refusal in Japanese Application No. 2019014120, dated Jan. 14, 2020, with English translation, 11 pages.
U.S. Appl. No. 16/367,791, filed Mar. 28, 2019 Pending, No. submitted on May 17, 2019.
U.S. Appl. No. 12/913,639, filed Oct. 27, 2010 U.S. Pat. No. 9,041,790 Issued, No. submitted on Aug. 30, 2019.
U.S. Appl. No. 13/095,175, filed Apr. 27, 2011 U.S. Pat. No. 9,075,225 Issued, No. submitted on Aug. 30, 2019.
U.S. Appl. No. 14/173,500, filed Apr. 28, 2015 Pending, No. submitted on Aug. 30, 2019.
U.S. Appl. No. 14/314,743, filed Jun. 25, 2014 U.S. Pat. No. 9,518,920 Issued, No. submitted on Aug. 30, 2019.
U.S. Appl. No. 14/698,532, filed Apr. 28, 2015 U.S. Pat. No. 9,720,217, Issued, No. submitted on Aug. 30, 2019.
U.S. Appl. No. 14/710,046, filed May 12, 2015 Pending, No. submitted on Aug. 30, 2019.
U.S. Appl. No. 15/066,065, filed Mar. 10, 2016 Pending, No. submitted on Aug. 30, 2019.
U.S. Appl. No. 15/360,724, filed Apr. 28, 2015 U.S. Pat. No. 9,989,750 Issued, No. submitted on Aug. 30, 2019.
U.S. Appl. No. 15/624,434, filed Apr. 28, 2015 U.S. Pat. No. 10,114,203 Issued, No. submitted on Aug. 30, 2019.
U.S. Appl. No. 15/995,598, filed Jun. 1, 2018 Pending, No. submitted on Aug. 30, 2019.
U.S. Appl. No. 16/113,578, filed Aug. 27, 2018 Pending, No. submitted on Aug. 30, 2019.
U.S. Appl. No. 16/367,791, filed Mar. 28, 2019 Pending, No. submitted on Aug. 30, 2019.
U.S. Appl. No. 16/439,333, filed Jun. 12, 2019 Pending, No. submitted on Aug. 30, 2019.
Japanese Office Action in Japanese Application No. 2016-522155, dated Nov. 7, 2019, 41 pages with English Translation.
U.S. Appl. No. 16/367,791, filed Mar. 28, 2019 Pending, No. submitted on Aug. 26, 2019.
U.S. Appl. No. 16/455,482, filed Jun. 27, 2019—Published 20190324258, No. submitted on Aug. 26, 2019.
U.S. Appl. No. 16/455,539, filed Jun. 27, 2019—Published 20190317309, No. submitted on Aug. 26, 2019.
U.S. Appl. No. 14/713,500, filed Feb. 5, 2014 Pending, No. submitted on Aug. 26, 2019.
U.S. Appl. No. 14/314,743, filed Jun. 25, 2014 U.S. Pat. No. 9,518,920 Issued, No. submitted on Aug. 26, 2019.
U.S. Appl. No. 15/066,065, filed Mar. 10, 2016 Pending, No. submitted on Aug. 26, 2019.
U.S. Appl. No. 15/360,724, filed Nov. 23, 2016 U.S. Pat. No. 9,989,750 Issued, No. submitted on Aug. 26, 2019.
U.S. Appl. No. 15/995,598, filed Jun. 1, 2018 Pending, No. submitted on Aug. 26, 2019.
European Communication Pursuant to Article 94(3) EPC issued in EP Application No. 14817587.0, dated Apr. 29, 2020, 5 pages.
Japanese Notice of Reasons for Refusal in JP Application No. 2019111995, dated Mar. 16, 2020, 11 pages with English Translation.
U.S. Appl. No. 16/455,482, filed Jun. 27, 2019, 2019/0324258 Published, No. submitted on Mar. 17, 2020.
U.S. Appl. No. 15/066,063, filed Mar. 10, 2016, U.S. Pat. No. 10,502,666 Issued, No. submitted on Mar. 17, 2020.
U.S. Appl. No. 16/367,791 filed Mar. 28, 2019 2019/0242794 Published, No. submitted on Mar. 17, 2020.
U.S. Appl. No. 14/173,500, filed Feb. 5, 2014, 2014/0152801 Published, No. submitted on Mar. 17, 2020.
U.S. Appl. No. 14/314,743, filed Jun. 25, 2014 U.S. Pat. No. 9,518,920 Issued, No. submitted on Mar. 17, 2020.

(56) References Cited

OTHER PUBLICATIONS

U.S. Appl. No. 15/360,724, filed Nov. 23, 2016 U.S. Pat. No. 9,989,750 Issued, No. submitted on Mar. 17, 2020.
U.S. Appl. No. 15/995,598, filed Jun. 1, 2018 U.S. Pat. No. 10,459,213 Issued, No. submitted on Mar. 17, 2020.
U.S. Appl. No. 16/455,539, filed Jun. 27, 2019 2019/0317309, No. submitted on Mar. 17, 2020.
U.S. Appl. No. 16/455,482, filed Jun. 27, 2015, 2019/0324258 Published, No. submitted on Mar. 17, 2020.
U.S. Appl. No. 15/066,065, filed Mar. 10, 2016, U.S. Pat. No. 10,502,666 Issued, No. submitted on Mar. 17, 2020.
Canadian Office Action issued in Canadian Application 2938896 dated Apr. 8, 2020, 21 pages.
U.S. Appl. No. 12/913,639, filed Oct. 27, 2010 U.S. Pat. No. 9,041,790 Issued, No. submitted on Mar. 17, 2020.
U.S. Appl. No. 14/698,532, filed Apr. 28, 2015 U.S. Pat. No. 9,720,217, Issued, No. submitted on Mar. 17, 2020.
U.S. Appl. No. 15/642,434, filed Jul. 6, 2017, U.S. Pat. No. 10,114,203 Issued, No. submitted on Mar. 17, 2020.
U.S. Appl. No. 16/113,578, filed Aug. 27, 2018 U.S. Pat. No. 10,354,564 Issued, No. submitted on Mar. 17, 2020.
U.S. Appl. No. 16/439,333, filed Jun. 12, 2019 U.S. Pat. No. 10,520,711 Issued, No. submitted on Mar. 17, 2020.
U.S. Appl. No. 16/701,078, filed Dec. 2, 2019, Pending, No. submitted on Mar. 17, 2020.
U.S. Appl. No. 13/095,175, filed Apr. 27, 2011, U.S. Pat. No. 9,075,225 Issued, No. submitted on Mar. 17, 2020.
U.S. Appl. No. 14/710,046, filed May 12, 2015 U.S. Pat. No. 10,620,234 Issued, No. submitted on Mar. 17, 2020.
U.S. Appl. No. 16/820,904, filed Mar. 17, 2020, Pending, No. submitted on Mar. 17, 2020.
U.S. Appl. No. 15/360,724, filed Nov. 23, 2016, U.S. Pat. No. 9,980,750 Issued, No. submitted on Mar. 17, 2020.
U.S. Appl. No. 16/455,539, filed Jun. 27, 2019, 2019/0317309 Published, No. submitted on Mar. 17, 2020.
U.S. Appl. No. 16/367,791, filed Mar. 28, 2019 U.S. Pat. No. 2019/0242794 Published, No. submitted on Mar. 17, 2020.

* cited by examiner

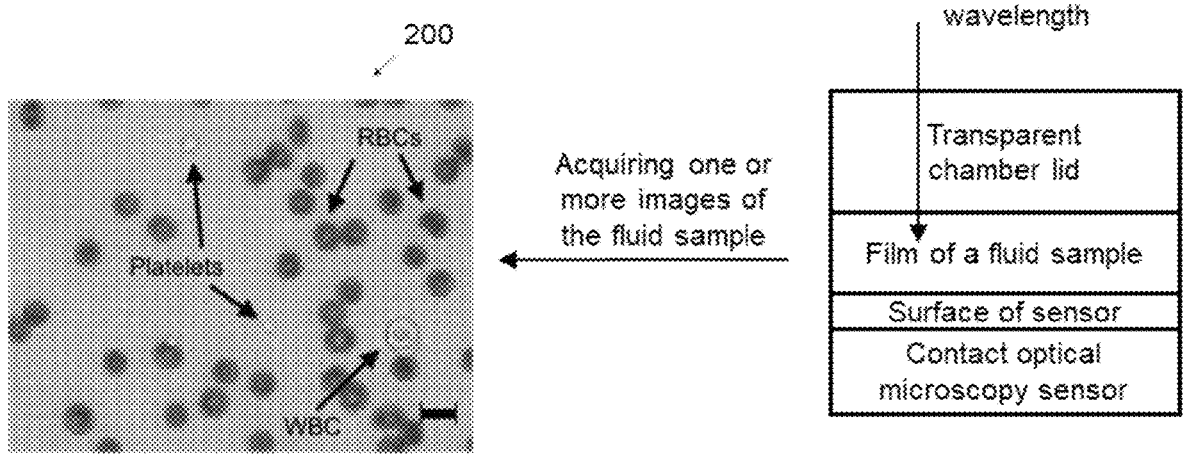

SAMPLE PROCESSING IMPROVEMENTS FOR QUANTITATIVE MICROSCOPY

PRIORITY CLAIMS AND RELATED APPLICATIONS

This application is a continuation and claims priority to U.S. patent application Ser. No. 15/066,065, filed Mar. 10, 2016, which is entitled to the benefit of the filing date of U.S. patent application 62/131,164, filed Mar. 10, 2015 and is a continuation-in-part of U.S. patent application Ser. No. 14/173,500, filed Feb. 5, 2014. This application is also a continuation-in-part of U.S. patent application Ser. No. 14/314,743, filed Jun. 25, 2014 (issued as U.S. Pat. No. 9,518,920 on Dec. 13, 2016), and is entitled to the benefit of the filing date of U.S. patent application 61/839,735, filed Jun. 26, 2013. Each of the patent applications identified above is incorporated here by reference in its entirety.

This application is also related to U.S. patent application Ser. No. 14/698,532, filed on Apr. 28, 2015, which claims the benefit of U.S. patent application Ser. No. 12/913,639 filed on Oct. 27, 2010 (now issued as U.S. Pat. No. 9,041,790 on May 26, 2015), which claims the benefit of U.S. provisional patent application 61/255,781, filed on Oct. 28, 2009 and is also related to U.S. patent application Ser. No. 14/710,046, filed on May 12, 2015, which claims benefit to U.S. patent application Ser. No. 13/095,175 filed on Apr. 27, 2011 (now issued as U.S. Pat. No. 9,075,225 on Jul. 7, 2015), which claims the benefit of Ser. No. 12/913,639 filed on Oct. 27, 2010 (now issued as U.S. Pat. No. 9,041,790 on May 26, 2015), which claims the benefit of U.S. provisional patent application 61/255,781, filed on Oct. 28, 2009. Each of the patent applications identified above is incorporated here by reference in its entirety.

FIELD

This specification generally describes technology related to sample processing for quantitative microscopy.

BACKGROUND

Complete blood count (CBC) and other diagnostic tests that measure hemoglobin (Hb) content of blood typically measure Hb via a spectroscopic system or a subsystem after lysing red blood cells (RBCs).

SUMMARY

Traditional techniques that measure Hb content of blood often add bulk and complexity to the measurement processing, creating a number of disadvantages that are salient for point-of-care (POC) diagnostic devices. For instance, such techniques often require significant sample preparation, which is often inaccessible in resource-limited regions where POC diagnostic devices are often used.

In general, in an aspect, a method for computing mean corpuscular hemoglobin can include: generating a diluted sample based on mixing a small sample of blood with one or more diluents; forming a thin film of the diluted sample on a surface of a contact optical microscopy sensor; illuminating red blood cells within a portion of the thin film of the diluted sample using light of a predetermined wavelength; acquiring one or more images of the diluted sample based on illuminating the red blood cells within the portion of the thin film of the diluted sample; processing the acquired one or more images of the diluted sample; and determining a value of mean corpuscular hemoglobin in the red blood cells within the portion of the thin film of the diluted sample based on processing the acquired images of the diluted sample.

One or more implementations may include the following optional features. For example, in some implementations, forming a thin film includes forming a thin film between a transparent chamber lid and the surface of the contact optical microscopy sensor.

In some implementations, forming a thin film between the lid and the contact optical microscopy sensor includes: placing the diluted sample on a surface of the contact optical microscopy sensor; and lowering the transparent chamber lid to a predetermined height determined by a spacer.

In some implementations, the size of the predetermined height is configured such that lowering of the transparent chamber lid onto the surface of the contact optical microscopy sensor (i) constrains the red blood cells to lie within a broadest dimension of the red blood cells parallel to the surface of the contact optical microscopy sensor, and (ii) does not result in structural damage to the red blood cells.

In some implementations, the one or more images of the diluted sample that are acquired include image features of at least one hundred red blood cells.

In some implementations, the predetermined wavelength comprises a wavelength that corresponds to a wavelength within the absorbance band of a form of hemoglobin with the highest extinction coefficient of that form of hemoglobin.

In some implementations, processing the acquired images of the diluted sample includes: estimating a background pixel value for each pixel within the respective acquired images; segmenting one or more regions within the respective acquired images that each contain exactly one red blood cell; and calculating the mean corpuscular hemoglobin based on the segmented one or more regions within the respective acquired images.

In some implementations, the generated diluted sample: has an isotonicity that is substantially equal to an isotonicity of red blood cells; has coagulation properties such that the generated diluted sample is less likely to coagulate compared to coagulation properties of red blood cells; and maintains a predetermined pH level of the generated diluted sample.

In some implementations, the acquired one or more images include at least a statistically significant number of the red blood cells in the diluted sample.

In some implementations, at least one of the one or more diluents comprises a nitrite.

In some implementations, generating a diluted sample comprises generating a diluted sample based on mixing the sample of blood with a diluent such that the mixing results in sphering of the red blood cells within the diluted sample.

In general, in an aspect, a method for computing a mean amount of a measured analyte within a fluid sample can include: forming a thin film of a fluid sample on a surface of a contact optical microscopy sensor, the fluid sample comprising particulate matter that includes an analyte to be measured, the analyte having a distinctive absorption spectrum; illuminating at least a portion of the thin film of the fluid sample using white light of a predetermined wavelength; acquiring one or more images of the fluid sample based on illuminating at least a portion of the thin film of the fluid sample using white light of a predetermined; wavelength; processing the acquired one or more images of the fluid sample; and determining a value of a mean amount of the analyte based on processing the one or more images of the fluid sample.

In some implementations, forming a thin film includes forming a thin film between a transparent chamber lid and the contact optical microscopy sensor.

In some implementations, forming a thin film between the lid and the surface of the contact optical microscopy sensor includes: placing the fluid sample on a surface of the contact optical microscopy sensor and lowering the transparent chamber lid to a predetermined height determined by a spacer.

In some implementations, the size of the predetermined height is configured such that lowering of the transparent chamber lid onto the surface of the contact optical microscopy sensor (i) constrains the particulate matter of the sample fluid to lie within a broadest dimension of the particular matter to the surface of the contact optical microscopy sensor, and (ii) does not result in structural damage to the particulate matter of the sample fluid.

In some implementations, processing the one or more acquired images includes: estimating a background pixel value for each pixel within the respective one or more acquired images; segmenting one or more regions within the respective acquired images that each contain exactly one particle; and calculating the mean amount of the analyte based on the segmented one or more regions within the respective acquired images.

In some implementations, forming a thin film includes: placing the fluid sample on the surface of the contact optical microscopy sensor; and enabling the thin film of the fluid sample formed on a surface of a contact optical microscopy sensor to settle.

These, and other aspects, features, implementations, and advantages may be expressed as methods, apparatus, systems, components, compositions, software products, methods of doing business, and in other ways.

These and other aspects, features, implementations, and advantages will become apparent from the following description and from the claims.

BRIEF DESCRIPTION OF THE DRAWINGS

FIG. 2 is a contact optical microscopy image of a blood cell.

In the drawings, like reference numbers represent corresponding parts throughout.

DETAILED DESCRIPTION

Figure 1:
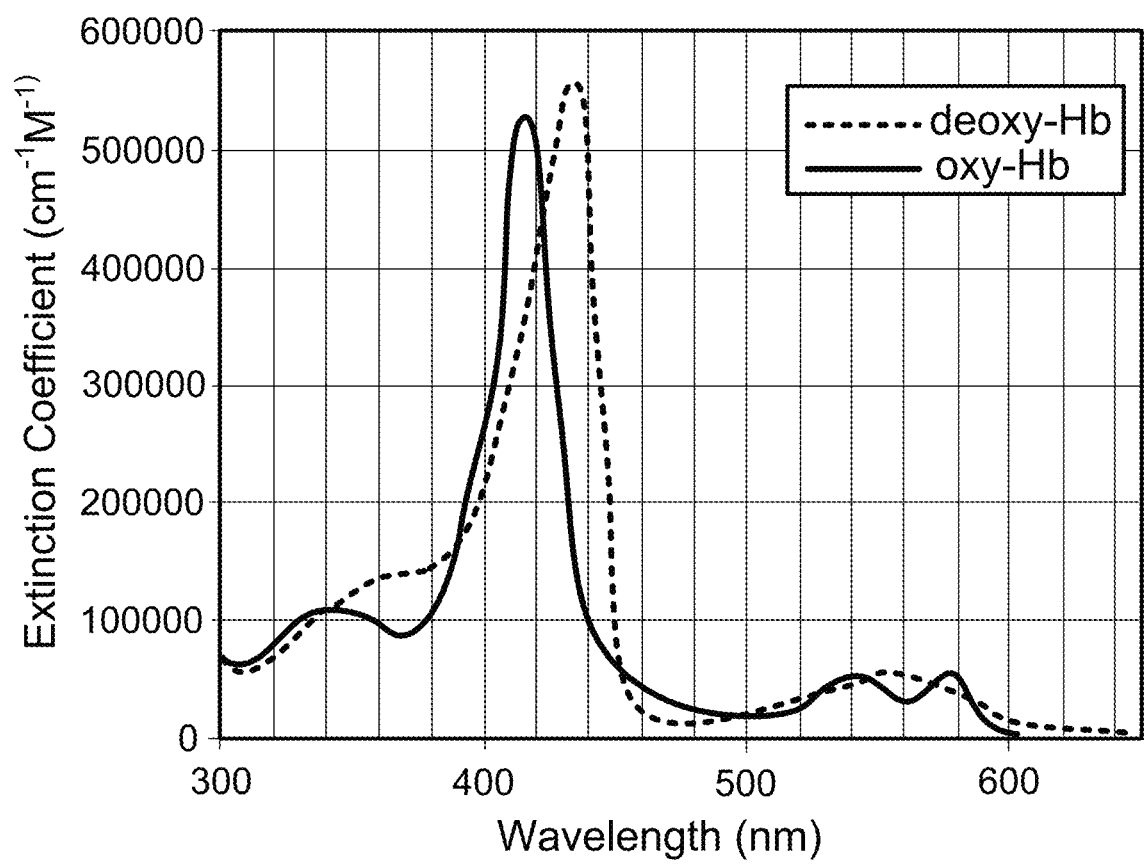
FIG. 1 is graph of hemoglobin absorption spectra.

In some examples, the bulk and complexity of the conventional CBC process can be overcome with the use of contact optical microscopy (COM)-based microspectrometry. In some instances, such techniques can also be implemented with optical lens microscopes. In COM-based microspectrometry, molecules in individual pixels and regions in a microscopic image are quantified using optical absorption measurements. COM-based microspectrometry permits measurement of the Hb content of individual RBCs within an image. This can then be averaged over a plurality of imaged RBCs to estimate the mean corpuscular hemoglobin (MCH). The estimation of MCH, along with mean corpuscular volume (MCV) and red blood cell concentration (RBC), both of which can be determined from the microscopy image, mean corpuscular hemoglobin concentration (MCHC) and concentration of hemoglobin in blood (Hgb), additional elements of the CBC, can then be derived.

To calculate the MCH from a COM image, microspectrometry must be used to initially quantify Hb content. Microspectrometry within lens-based microscopy has existed for many decades and has been performed previously on RBCs. In 1960, Sondhaus & Thorell published a study in which the Hb absorbance spectra from sub-areas of RBCs were examined, exploring the correlation of RBC maturity and Hb and free-iron content [C. A. Sondhaus and B. Thorell, "Microspectrophotometric Determination of Nonheme Iron in Maturing Erythroblasts and its Relationship to the Endocellular Hemoglobin Formation," *Blood*, vol. 16, no. 3, pp. 1285-97, 1960]. Tsujita et al. measured the change of the absorbance spectrum within RBCs depending the presence of nitric oxide [K. Tsujita, T. Shiraishi, and K. Kakinuma, "Microspectrophotometry of nitric oxide-dependent changes in hemoglobin in single red blood cells incubated with stimulated macrophages," *J. Biochem.*, vol. 122, no. 2, pp. 264-70, August 1997]. Meletis et al. attempted to measure MCH using lens-based transmission microspectrometry [J. Meletis, X. Yataganas, G. Eliopoulos, J. Panourgais, D. Loukopoulos, and P. Fessas, "Hemoglobin Content of Single Erythrocytes from Fetuses with Parents Having Heterozyhous ß-Thalassemia," *Acta Haematol.*, vol. 73, pp. 16-21, 1985]. Blood was spread on a glass slide, and 50-100 RBCs in each sample were measured by illuminating them with 415 nm light, dividing the full area of each RBC into 0.5 µm pixels, and measuring absorbance at each pixel. This process was slow (60-90 minutes per test), and results, though well correlated with those obtained using ordinary instruments based on spectroscopy of lysed blood ($R^2=0.87$) were unacceptably variable (coefficient of variation, CV=28%).

Some of this variability is due to the small number of RBC within a standard high magnification field of view. COM, however, yields high magnification over a very large field of view that can include large numbers of RBCs. In addition, lens-based microspectrometry for quantification of absorbing molecules is also sensitive to focal plane alignment relative to the RBCs, since light transmitting through Hb that is outside the focal plane may not be collected. Thus, for example, the depth of focus of the objective lens used by Meletis et al. was <0.5 µm, which is much thinner than an RBC (typically 1.1 µm thick at the center and 2.6 µm thick at the torus-shaped outer band [K. G. Engstrom and E. Löfvenberg, "Treatment of Myeloproliferative Disorders With Hydroxyurea: Effects on Red Blood Cell Geometry and Deformability," *Blood*, vol. 91, no. 10, pp. 3986-3991, 1998]), meaning parts of every RBC measured were out of focus, so that part of the Hb signal can be blurred outside the cell borders and lost. COM, on the other hand, has no focal plane—COM produces very little blurring of objects less than a few microns from the imaging surface—so can outperform standard microspectrometry for MCH measurement.

Standard optical spectrometry measures the quantity of a light-absorbing analyte dispersed in a solution using Beer's law:

$$\frac{I}{I_0} = 10^{\wedge}(-\epsilon C \ell) \qquad (1)$$

where $I_0$ is the incident light intensity, I is the transmitted light intensity, $\in$ is the extinction coefficient (molar absorptivity) of the absorber (Hb in this case) at the incident wavelength, C is the molar concentration of the absorber in the solution, and $\ell 0$ is the path length through the solution. Extinction is caused by light either being scattered or lost to true absorption, where the energy is converted to another form. Microspectrometry relies on Beer's law, but applies it to images of microscale objects to calculate the absorber's concentration within that object.

The following derivation of the relationship between MCH and Beer's law depends on the following simplifying assumptions:
1. The cell in question causes no reflection, refraction, or scattering.
2. Only one Hb form is present, meaning E is known.
3. There is uniform [Hb] concentration inside the RBC and negligible [Hb] outside the RBC.
4. Within a given pixel, the RBC thickness, $\ell$, is uniform.

The validity of these assumptions is addressed below.

For each pixel covered by an RBC, the following two equations are defined:

$$C = [Hb] = \frac{Hb_p}{V} \quad (2)$$

$$V = d^2 * \ell \quad (3)$$

where $Hb_p$ is the number of moles of Hb in the column above the pixel, V is the volume of the RBC portion directly above the pixel, and d is the pixel side-length. The 2$^{nd}$ equation assumes that $\ell$ is constant over the entire pixel. These two definitions are substituted into Beer's law to yield:

$$\frac{I_p}{I_{0,p}} = 10^\wedge\left(-\epsilon\left(\frac{Hb_p}{d^2\ell}\right)\ell\right) \quad (4)$$

where $I_p$ is the measured intensity of the pixel and $I_{0,p}$ is the estimated background intensity, i.e., the intensity expected if no RBC was present. The above equation is not sensitive to $\ell$, which is useful because path length is not known. The [Hb] term has also been eliminated, which too is not directly measureable in a COM image. Equation (4) is rearranged, yielding $$\log\frac{I_p}{I_{0,p}} = -\epsilon\frac{Hb_p}{d^2} \quad (5)$$

Converting moles of Hb to mass of Hb via a simple unit conversion, $m_{Hb,p} = M_{Hb} * Hb_p$, where $M_{Hb}$ is the molar mass, and solving for $m_{Hb,p}$ yields the mass of Hb above the pixel.

$$m_{Hb,p} = \frac{M_{Hb}d^2}{\epsilon}\log\left(\frac{I_{0,p}}{I_p}\right) \quad (6)$$

This is summed over all the pixels in the RBC, yielding $$m_{Hb,RBC} = \sum_{p=1}^{P}\frac{M_{Hb}d^2}{\epsilon}\log\left(\frac{I_{0,p}}{I_p}\right) \quad (7)$$

where P is the total number of pixels covered by the RBC. Once $m_{Hb,RBC}$ is calculated for N RBCs in the image, the mean is taken to yield the MCH:

$$MCH = \frac{M_{Hb}d^2}{N\epsilon}\sum_{n=1}^{N}\sum_{p=1}^{P_n}\log\left(\frac{I_{0,np}}{I_{np}}\right) \quad (8)$$

In the MCH equation above, $M_{Hb}$, d, and E are known constants. $I_{np}$, $I_{0,np}$, $P_n$, and N and are outputs from computer vision described below.

To increase the signal-to-noise ratio of the intensity measurements, it is preferable to illuminate Hb at a wavelength where its extinction coefficient is as high as possible. This gives maximum separation of I and $I_0$, maximizing signal. The absorbance maxima for Hb occur in the violet region of the visible spectrum (400-430 nm).

As depicted in FIG. 1, different varieties of Hb have different absorption spectra and maxima. Oxygenated hemoglobin (oxy-Hb) and deoxygenated hemoglobin (deoxy-Hb) both exist in blood. The blood oxygenation of Hb, i.e., the percentage of Hb in oxy-Hb form, can vary in the human body from 60% (venous blood) to ~100% (arterial blood). The vast majority of the remaining Hb exists in deoxy-Hb form, except in cases of blood poisoning. The $MCH_{COM}$ could depend on the oxygenation percentage and thus differ from the true MCH.

Though oxy- and deoxy-Hb have different absorbance profiles, it was suspected that in a real POC test, the vast majority of the Hb would be oxygenated while the blood droplet waited on a finger. If it is assumed that Hb is fully oxygenated, then $\epsilon_{oxy-Hb}$ has a maximum value of $5.243*10^5$ cm$^{-1}$M$^{-1}$, occurring at 415 nm. Substituting this value into Equation (8), as well as $M_{Hb}$=64 500 g/mol [S. Prahl, "Optical Absorption of Hemoglobin," *Oregon Medical Laser Center*, 1999. [Online]. Available: http://omlc.org/spectra/hemoglobin/. [Accessed: 15 Feb. 2013].] and d=1.1 µm (the pixel size of the COM sensor used in this research) yields:

$$MCH = \frac{1.49}{N}\sum_{n=1}^{N}\sum_{p=1}^{P_n}\log\left(\frac{I_{0,np}}{I_{np}}\right) \quad (9)$$

Note that the illumination wavelength distribution can alter this coefficient. LEDs commonly have full-width-half-maxima of 5 nm and 10 nm, whereas the extinction peaks have full-width-half-maxima of ~20 nm. As a result, using the extinction maximum is a reasonable approximation, even if the LED wavelength peak is off by 2 nm or so. Apart from improving the absorbance signal, a second advantage of selecting the extinction maximum is that the signal is less sensitive to small deviations in LED wavelength, since the slope at the peak is 0 (though the drop-off away from the peak is steep, so this effect is limited). A sample COM image obtained using 415 nm illumination is depicted in FIG. 2.

As depicted in FIG. 2, violet illumination results in good contrast for RBCs in comparison to platelets and WBCs. Contrast also aids in machine-based RBC segmentation and counting, since RBCs are easily distinguished from other objects in the image.

It is assumed in the above analysis that all Hb is converted to oxy-Hb. If this is not the case, the MCH correlation is likely to be poor. However, there are different ways to address this potential problem.

One solution is to illuminate the blood at the maximum oxy/deoxy-Hb isosbestic point, 422 nm. Isosbestic points are wavelengths where both forms of Hb have equal absorbance. However, LEDs are not easily found at this wavelength. To predict the effect of off-isosbestic illumination, the ratio of measured milt, to true milt, can be calculated, where the measured milt, is calculated under the assumption of full oxygenation. The $m_{Hb,measured}$ is inversely proportional to $\epsilon_{Hb}$, as seen in Equation (6), meaning that the mass measurement of any deoxy Hb will be off by a factor of $\epsilon_{deoxy-Hb}/\epsilon_{oxy-Hb}$, the ratio of true extinction to presumed extinction. To calculate the mass ratio, the mass fractions of oxy-Hb and deoxy-Hb should be added together but with the deoxy-Hb fraction multiplied by the ratio of the extinction coefficients:

$$\frac{m_{Hb,measured}}{m_{Hb,true}} = f + \frac{\epsilon_{deoxy-Hb}}{\epsilon_{oxy-Hb}}(1-f) \qquad (10)$$

where f is the oxy-Hb fraction, set to 0.6 in the worst case. Converting the mass ratio to a percent difference is straightforward, and the result is obtained that if the illumination is even 1 nm off the isosbestic point in either direction, the resulting Hb mass measurement will off be up to 4%. This is due to the sharply opposing slopes of the oxy/deoxy-Hb absorbance. A wavelength tolerance of <1 nm may be achievable with appropriate illumination sources and optical filters, but a simpler solution is available, as described below.

There are other isosbestic points with less severe differences in slopes, such as 390 nm, but these have much lower absorbance, reducing RBC contrast. They may be useful, but would be more difficult from a computer-vision perspective.

Another possibility is to chemically convert both oxy-Hb and deoxy-Hb to a third, single form. StP instruments typically convert all Hb to carboxyhemoglobin (CO-Hb) or methemoglobin (met-Hb) after lysing the RBCs. For Hb microspectrometry, Hb needs to be converted within the cell, without damaging the membrane, during a reasonably short incubation time. Fortunately, sodium nitrite ($NaNO_2$) is a suitable conversion agent. Sodium nitrite can pass through the RBC membrane, and it converts both oxy- and deoxy-Hb to met-Hb. Met-Hb is hemoglobin whose iron ions have an oxidation state of 3+, instead of the normal 2+. Oxygen does not bind to met-Hb. Met-Hb has an absorbance maximum at 405 nm with a 10-20% higher extinction coefficient compared to oxy-Hb [C. Donadee, N. J. H. Raat, T. Kanias, J. Tejero, J. S. Lee, E. E. Kelley, X. Zhao, C. Liu, H. Reynolds, I. Azarov, S. Frizzell, E. M. Meyer, A. D. Donnenberg, L. Qu, D. Triulzi, D. B. Kim-Shapiro, and M. T. Gladwin, "Nitric oxide scavenging by red blood cell microparticles and cell-free hemoglobin as a mechanism for the red cell storage lesion," Circulation, vol. 124, no. 4, pp. 465-76, July 2011]. Assuming the maximum extinction coefficient for met-Hb is 15% higher than that of oxyHb, the MCH equation becomes:

$$MCH = \frac{1.28}{N}\sum_{n=1}^{N}\sum_{p=1}^{P_n}\log\left(\frac{I_{0,np}}{I_{np}}\right) \qquad (11)$$

Blood and Power [30] showed that conversion of both oxy-Hb and deoxy-Hb to met-Hb in live RBCs is also relatively rapid, particularly when both oxy-Hb and deoxy-Hb species exist in the blood: maximum [met-Hb] was reached after 20 minutes with an initial 1:12 nitrite:heme ratio (heme being the oxygen binding subunit of Hb, of which there are four per molecule), and was followed by [metHb] decreasing slowly due to methemoglobin reductase activity and reaction with nitric oxide, the byproduct of methemylation of deoxy-Hb [A. B. Blood and G. G. Power, "In vitro and in vivo kinetic handling of nitrite in blood: effects of varying hemoglobin oxygen saturation," Am. J. Physiol. Heart Circ. Physiol., vol. 293, pp. H1508-17, September 2007].

At normal venous blood oxygenation of 60%, the worst-case scenario for capillary blood, approximately 100% conversion to met-Hb is achieved after 60 seconds (using purified Hb) [R. Grubina, Z. Huang, S. Shiva, M. S. Joshi, I. Azarov, S. Basu, L. a Ringwood, A. Jiang, N. Hogg, D. B. Kim-Shapiro, and M. T. Gladwin, "Concerted nitric oxide formation and release from the simultaneous reactions of nitrite with deoxy- and oxyhemoglobin," J. Biol. Chem., vol. 282, no. 17, pp. 12916-27, April 2007]. Therefore, conversion efficiency and rate is not likely to be an issue.

Methemylation is therefore seen as a viable option for improving the reliability of COM-based microspectrometry. Using nitrite in large excess is posited to rapidly convert all of the Hb within cells and hold it at the maximum concentration longer than required for a COM experiment.

In order to obtain consistently precise estimates of the MCH, it must be ensured that a sufficient number of countable RBCs are present in any COM image.

The standard error of the mean of measurements drawn from a Gaussian distribution is $$e = \sigma/\sqrt{N} \qquad (12)$$

where $\sigma$ is the standard deviation and N is the number of measurements. Assuming that $m_{Hb,RBC}$ follows a Gaussian distribution between RBCs, this equation can be applied to the MCH measurement, where N is the number of RBCs sampled for the calculation of the MCH. Thus, "$CV_{MCH,sampling}$", the CV of $e_{MCH}$, is given by:

$$CV_{MCH,sampling} = \frac{e_{MCH}}{MCH}*100 = \frac{\sigma_{mHb,RBC}}{MCH\sqrt{N}}*100 = \frac{CV_{mHb,RBC}}{\sqrt{N}} \qquad (13)$$

where $\sigma_{mHb,RBC}$ is the standard deviation of the $m_{Hb,RBC}$ measurements (MCH is the mean of these measurements). Solving for N yields:

$$N = \left(\frac{CV_{mHb,RBC}}{CV_{MCH,sampling}}\right)^2 \qquad (14)$$

Assuming a worst-case $CV_{mHb,RBc}$ of 50% (which would be highly clinically abnormal), to achieve an ideal value of $CV_{MCH,sampling}<1\%$, making it essentially negligible with respect to a target $CV_{MCH}$ of 5%, at least 2000 RBCs need to be sampled, as calculated by substituting these two values into Equation (14).

At roughly 50 pixels per RBC and 8 million pixels in the field-of-view of an 8 megapixel sensor with 1.1 μm pixel pitch, well over 10 000 RBCs can be included the field of view while still leaving most of the area as background (which allows for more straightforward calculation of $I_0$).

Beer's law relies on several assumptions that do not necessarily hold true in Hb microspectrometry. This can lead to an overall bias, cell-to-cell variation, or person-to-person variation in MCH calculations, the latter because blood from different persons can have different characteristics. Bias is correctable, and the number of RBCs counted is so large that the error of the estimate of the mean $m_{Hb,RBC}$ will be small, as described above. Person-to-person variation is therefore of the most concern, as this would weaken the correlation between MCH measured by COM and by current standard-of-practice (StP)

Beer's law assumes that there are no scattering or absorption events caused by materials in the blood film other than Hb itself. However, material inside or outside the RBC may also scatter or absorb. These events may lead to underestimation of the MCH, the effect is likely small, as Hb has much higher absorbance than any other blood/diluent component at the wavelengths in question [A. Airinei and A. Sadoveanu, "Spectrophotometric Analysis of the Blood Plasma," *Rom. J. Biophys.*, vol. 16, no. 3, pp. 215-20, 2006][M. De, S. Rana, H. Akpinar, 0. R. Miranda, R. R. Arvizo, U. H. F. Bunz, and V. M. Rotello, "Sensing of proteins in human serum using conjugates of nanoparticles and green fluorescent protein," *Nat. Chem.*, vol. 1, no. September, pp. 461-5, 2009].

Reference physiological "free" [Hb] (Hb concentration in the plasma) is as high as 5 µM [N. Na, J. Ouyang, Y. E. C. Taes, and J. R. Delanghe, "Serum free hemoglobin concentrations in healthy individuals are related to haptoglobin type," *Clin. Chem.*, vol. 51, no. 9, pp. 1754-5, September 2005], while reference MCHC values are as low as 5000 µM [N. Beck, *Diagnostic Hematology*. London: Springer London, 2009], three orders of magnitude higher than the image background. Thus free plasma is normally negligible in the MCH calculation. The assumption of negligible [Hb] outside RBCs may be false if significant hemolysis is present. Free [Hb] can rise to 10 µM during severe sepsis [M. Adamzik, T. Hamburger, F. Petrat, J. Peters, H. de Groot, and M. Hartmann, "Free hemoglobin concentration in severe sepsis: methods of measurement and prediction of outcome," *Crit. Care*, vol. 16, no. 4, July 2012] or 25 µM during a sickle cell anemia crisis [D. J. Schaer, P. W. Buehler, A. I. Alayash, J. D. Belcher, and G. M. Vercellotti, "Hemolysis and free hemoglobin revisited: exploring hemoglobin and hemin scavengers as a novel class of therapeutic proteins," *Blood*, vol. 121, no. 8, pp. 1276-84, February 2013]. This, however, is still at least two orders of magnitude smaller than the lowest levels of MCHC, so it is still negligible.

The general method for measuring the MCH on a drop blood using COM is as follows:
1. A drop of blood is mixed and incubated briefly with an appropriate diluent.
2. The blood mixture is injected into the specimen chamber, forming a thin film between the COM sensor and a transparent chamber lid.
3. Multiple images are acquired while light of a specific wavelength is transmitted through the chamber lid to illuminate the cells.
4. The images are processed and analyzed by a computer-vision algorithm to extract the MCH.
5. The specimen chamber is cleaned.

To test the central hypothesis, several blood samples from different individuals were tested on both a single COM device and an StP machine. The data were compared using regression analysis to determine suitable correlation parameters, the coefficient of determination (R2), and the CV of the residuals.

Two diluents were prepared for the experiments, to be mixed with blood at a 3:1 diluent:blood ratio. Diluent N, which included NaNO2, contained the following components dissolved in distilled water:
1. 112.3 mM NaNO2
2. 6.5 mM Brilliant Cresyl Blue stain (Sigma, 860867)
3. 21.3 mM Disodium EDTA (EM Science, EX0539-1)
4. 5.87 mM HEPES (Sigma, H4034)
5. 5.57 mM KCl
6. 7.36 mM NaCl Diluent xN, which excluded NaNO2, contained the following components dissolved in distilled water:
1. 6.5 mM Brilliant Cresyl Blue stain (1% w/w)
2. 21.3 mM Disodium dihydrate EDTA
3. 5.87 mM HEPES
4. 5.57 mM KCl
5. 118.6 mM NaCl The key component of Diluent N diluent was NaNO2, used to convert oxy-Hb and deoxy-Hb to met-Hb. Diluents N and xN were identical except for the replacement in Diluent xN of NaNO2 with a molar equivalent of NaCl. The Brilliant Cresyl Blue stain was included for experiments that are beyond the scope of this research. The diluent was designed to fulfill several functions to ensure that the cells maintained their health and form:
1. Isotonicity, to maintain cell shape and health, was achieved using appropriate concentrations of NaCl, KCl, and NaNO2 in the diluents.
2. Anticoagulation prevents blood cells from aggregating irreversibly, which makes counting them difficult. Ethylenediaminetetraacetic acid (EDTA) was included as an anticoagulant.
3. The diluent was buffered at physiological pH (~7.4) using the HEPES buffer.

In some cases the diluent is chosen to achieve sphering of the red blood cells. It may be advantageous if the spacer (chamber height) is small enough (<3 µm) so that the resulting spherical red blood cells are compressed into a more-or-less cylindrical shape by the lowered chamber-lid, to provide an approximately uniform path length for the collimated light and to simplify the determination of cell volume. The sphering agent can comprise inclusion of a surfactant such as sodium dodecyl sulfonate or hexadecyl trimethyl ammonium chloride. (See US patent application publication 2009/0258338).

Diluents were used to dilute a small blood sample at a 3:1 diluent:blood ratio. A thin film of this mixture was then formed by placing a drop between a glass slide and a glass coverslip. This film was examined using transmission microscopy to ensure that the cells were not damaged by the diluent. Cells using diluents N and xN diluents appeared very similar to cells in blood diluted using other formulations that met the requirements described above. In an acceptable diluent formulation, RBCs appear quite circular, with few having bulges or wrinkles. Also, almost all RBCs have light centers surrounded by a darker band. This indicates biconcavity, since the thinner cell center absorbs less light. Further, lack of coagulation is indicated by the individual cells appearing fairly evenly distributed and without stacking.

The COM sensor used was an Omnivision OV8850, with 1.1 µm square pixels. Bayer color filters were removed by reactive-ion etching.

A transparent chamber lid was used to form the thin blood film on the COM sensor. A drop of blood:diluent mixture was placed on the sensor, and the chamber lid was gently lowered onto the sensor surface to a height of ~3.5 µm, with the height set using a spacer. This forced most of the blood mixture out the sides, leaving a small film of fluid remaining in the gap to be imaged.

The chamber height was not measured precisely. However, typical RBC have a maximum thickness of 2.6 µm, so even if the chamber height varied by 20%, the chamber lid should not squash any RBCs. This height should cause the RBCs to lie flat though, as they have typical diameters 7.5 µm [Y. Park, C. a Best, T. Auth, N. S. Gov, S. a Safran, G. Popescu, S. Suresh, and M. S. Feld, "Metabolic remodeling of the human red blood cell membrane," PNAS, vol. 107, no. 4, pp. 1289-94, January 2010]. When the chamber lid was well seated, RBC stacking (rouleaux) was not observed.

The illuminator for the blood images consisted of two LEDs: a 405 nm LED (Mouser Electronics, 749-UV3TZ-405-15), a 415 nm LED (Lumex, SSL-LXT046UV3C).

Experiment 1: Using Diluent N (nitrite-included) and 405 nm light, blood samples from 15 different individuals were each tested once on the StP. These 15 samples were tested between two and four times each using COM.

Experiment 2: The final six samples used in Experiment 1 were also tested using COM and Diluent xN (nitrite-free) with 415 nm illumination, with between one and four COM tests per sample. For these six samples, the Experiment 2 tests were performed prior to the Experiment 1 tests because the former are likely to be more sensitive to oxygen contamination.

For the MCH calculations, all images were processed identically. Four violet images were averaged together to reduce noise, and the 20-frame averaged 6 ms-exposure darkframe was subtracted, yielding a single master image. The computer-vision algorithm consisted of three steps:
1. Estimate the background value for every pixel in the image
2. Segment regions containing exactly one RBC (image segmentation)
3. Calculate the MCH using Equation (8)

In each RBC segmentation, the background level calculated for each pixel was assigned to I0,np in Equation (8). For the image segmentation of step 2, a COM image was first thresholded to produce a binary mask. Objects greater than 1.5× or less than 0.5× the mean RBC size were eliminated. This eliminated the vast majority of noise, artifacts, RBC clusters, and occasional pixels from non-RBC objects. The remaining objects became the RBC segmentations for the MCH calculation. Step 3 took the intensity values for the pixels in each RBC segmentation and scanned over them, applying the MCH equations described above. Equation (11) was used with Diluent N, and Equation (9) was used for Diluent xN.

Data acquisition and analysis in comparison with StP showed that the results of the Diluent xN tests and the corresponding Diluent N tests were somewhat similar. Both met the CVMCH, target requirement, with similar CVMCH's of 2.27% and 3.38% respectively. For these subjects, the correlation between COM and StP measurements was very strong for both Diluent N and xN, with R2 values of 0.96 and 0.98 respectively.

Variation in MCHCOM measurements depends on several factors, one of which is RBC shape, presumably due to violations of the Beer's law assumptions discussed above. Thus measurements of MCH, as well as of MCV, can be improved by converting the RBCs from dicoid to spherical shape [Kim Y R, Ornstein L: Isovolumetric sphering of erythrocytes for more accurate and precise cell volume measurement by flow cytometry. Cytometry 4:419, 1983] and various US patents [e.g., Fan et al., 1997 U.S. Pat. No. 5,633,167 and patents cited therein]. If the chamber (i.e., spacer) height is less than the diameter of the sphered RBCs, they will be compressed into cylinders of uniform thickness.

Other implementations are within the scope of the following claims. For example, the described approach is not restricted to measurements of hemoglobin in red blood cells, but can be used to measure any substance that has a distinctive absorbance spectrum, in any cell or particle (so, for example in principle, for monitoring production of biopharmaceutical compounds by genetically engineered yeast cells).

What is claimed is:

1. A method comprising:
    placing a fluid sample on a surface of a contact optical microscopy sensor, the fluid sample comprising particulate matter that includes an analyte to be measured, the analyte having a distinctive absorption spectrum;
    forming a film of the fluid sample between a transparent chamber lid and the surface of the contact optical microscopy sensor by moving the transparent chamber lid to a predetermined distance from the surface of the contact optical microscopy sensor, the distance determined by a spacer, the moving of the transparent lid to the predetermined distance causing the particulate matter of the fluid sample to be compressed into a shape to provide a uniform path length for light passing through the particulate matter;
    acquiring one or more images of the fluid sample based on illuminating at least a portion of the film of the fluid sample using light of a predetermined wavelength,
    processing the acquired one or more images of the fluid sample; and
    determining a mean amount of the analyte based on the processing of the one or more images of the fluid sample by a processor.

2. The method of claim 1, in which the particulate matter of the fluid sample is compressed into a cylindrical shape.

3. The method of claim 1, wherein a magnitude of the predetermined distance is such that lowering of the transparent chamber lid onto the surface of the contact optical microscopy sensor (i) constrains the particulate matter of the fluid sample to lie parallel to the surface of the contact optical microscopy sensor, and (ii) does not result in structural damage to the particulate matter of the fluid sample.

4. The method of claim 1, wherein processing the one or more acquired images comprises:
    segmenting one or more regions within the respective acquired images that each contain exactly one particle; and
    calculating the mean amount of the analyte based on the segmented one or more regions within the respective acquired images.

5. The method of claim 1, wherein forming the film comprises:
    placing the fluid sample on the surface of the contact optical microscopy sensor; and
    enabling the fluid sample placed on the surface of a contact optical microscopy sensor to settle.

6. The method of claim 1, wherein the acquired one or more images include at least a statistically significant number of particles in the fluid sample.

7. The method of claim 1, wherein the predetermined wavelength is based on extinction coefficients of wavelengths within an absorbance band of the analyte.

8. The method of claim 1, wherein the analyte comprises hemoglobin.

9. The method of claim 8, wherein the fluid sample comprises oxygenated hemoglobin and deoxygenated hemoglobin, and the method further comprises converting both types of hemoglobin to a third type of hemoglobin.

10. The method of claim 1, comprising mixing the fluid sample with a diluent to generate a diluted sample.

11. The method of claim 10, wherein the diluent comprises a nitrite.

12. The method of claim 10, wherein the fluid sample comprises blood, and wherein generating a diluted sample comprises mixing the sample of blood with a diluent such that the mixing results in sphering of red bloods cells within the diluted sample.

13. The method of claim 10, wherein the fluid sample comprises blood, and wherein the generated diluted sample has at least two of the following properties:
   has an isotonicity that is substantially equal to an isotonicity of red blood cells;
   has coagulation properties such that the generated diluted sample is less likely to coagulate compared to coagulation properties of red blood cells; and
   maintains a predetermined pH level of the generated diluted sample.

14. The method of claim 1, wherein the mean amount of the analyte is an average mass of hemoglobin per red blood cell in the fluid sample.

15. The method of claim 1, comprising determining the mean amount of the analyte with a coefficient of variation of less than 1 percent.

16. The method of claim 1, in which processing the acquired one or more images of the fluid sample comprises performing a calculation based on a measured intensity of the light of the predetermined wavelength at the surface of the contact optical microscopy sensor, the calculation including an assumption that the path length for light passing through the particulate matter is uniform within each pixel of the contact optical microscopy sensor.

* * * * *

UNITED STATES PATENT AND TRADEMARK OFFICE
CERTIFICATE OF CORRECTION

| | | |
|---|---|---|
| PATENT NO. | : 10,768,078 B2 | Page 1 of 1 |
| APPLICATION NO. | : 16/367791 | |
| DATED | : September 8, 2020 | |
| INVENTOR(S) | : Alan Marc Fine and Hershel Macaulay | |

It is certified that error appears in the above-identified patent and that said Letters Patent is hereby corrected as shown below:

On the Title Page

Item (72), delete "Bedford (CA)" and insert -- Cambridge (MA) --, therefor.

On page 2, Item (60), Column 1, Line 7-9 delete "2013, provisional application No. 61/785,762, filed on Mar. 14, 2013, provisional application No. 67/761,467, filed on Feb. 6, 2013." and insert -- 2013. --, therefor.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*